(12) United States Patent
Xu et al.

(10) Patent No.: US 12,741,016 B2
(45) Date of Patent: Sep. 22, 2026

(54) C-TERMINUS MODIFIED HUMAN PAPILLOMA VIRUS TYPE 6 L1 PROTEIN AND USE THEREOF

(71) Applicant: INSTITUTE OF BASIC MEDICAL SCIENCES, CHINESE ACADEMY OF MEDICAL SCIENCES, Beijing (CN)

(72) Inventors: Xuemei Xu, Beijing (CN); Baicheng Xia, Beijing (CN); Ting Zhang, Beijing (CN)

(73) Assignee: Chinese Academy of Medical Sciences, Beijing (CN)

( * ) Notice: Subject to any disclaimer, the term of this patent is extended or adjusted under 35 U.S.C. 154(b) by 682 days.

(21) Appl. No.: 18/254,154

(22) PCT Filed: Sep. 26, 2021

(86) PCT No.: PCT/CN2021/120516
§ 371 (c)(1),
(2) Date: May 23, 2023

(87) PCT Pub. No.: WO2022/111020
PCT Pub. Date: Jun. 2, 2022

(65) Prior Publication Data

US 2024/0000909 A1 Jan. 4, 2024

(30) Foreign Application Priority Data

Nov. 26, 2020 (CN) ......................... 202011347629.5

(51) Int. Cl.
*A61K 39/00* (2006.01)
*A61P 37/04* (2006.01)

(52) U.S. Cl.
CPC .......... *A61K 39/0008* (2013.01); *A61P 37/04* (2018.01); *A61K 2039/5258* (2013.01)

(58) Field of Classification Search
None
See application file for complete search history.

(56) References Cited

U.S. PATENT DOCUMENTS 5,738,853 A 4/1998 Ludmerer et al.
2024/0000915 A1* 1/2024 Xu .......................... C12N 7/00

FOREIGN PATENT DOCUMENTS

CN 103819543 A 5/2014
CN 104710515 A 6/2015
CN 106831960 A 6/2017

OTHER PUBLICATIONS

Zhou et al. (Virology. 1991; 185: 625-632).*
(Continued)

*Primary Examiner* — Shanon A. Foley
(74) *Attorney, Agent, or Firm* — Fuller IP Law LLC; Rodney J. Fuller

(57) ABSTRACT

The present application relates to a C-terminus modified human papillomavirus type 6 L1 protein and use thereof. Specifically, the present application relates to a C-terminus modified human papillomavirus (HPV) type 6 L1 protein, an encoded nucleotide thereof, a vector comprising the nucleotide, a cell comprising the vector, a pentamer or virus-like particle composed of the HPV6 L1 protein, a vaccine containing the pentamer or virus-like particle and a vaccine adjuvant, and the use thereof in prevention of HPV infection and HPV infection-related diseases.

12 Claims, 3 Drawing Sheets

Specification includes a Sequence Listing.

(56) References Cited

OTHER PUBLICATIONS

Alignment of SEQ ID No. 1 with Geneseq database accession No. AAB98397 in WO200141799 by Sette et al. 2007.*
Farmer et al. (Recent Results Cancer Res. 2021 ; 217: 157-195).*
Chen et al. (Journal of Molecular Biology. 2001; 307: 173-182).*
Tori et al. (Journal of Bacteriology. 2011; 193 (8): 2035-2041).*
Garcea et al. ("Papillomavirus Structure and Assembly". In: Garcea, R.L., DiMaio, D. (eds) The Papillomaviruses. 2007; Springer, Boston, MA).*
Sun, Bo et al., "Development a scalable production process for truncated human papillomavirus type-6 L1 protein using WAVE Bioreactor and hollow fiber membrane", Appl Microbiol Biotechnol, pp. 1-10 (Oct. 8, 2015).

* cited by examiner

SEQUENCE LISTING

```
<160> NUMBER OF SEQ ID NOS: 43

<210> SEQ ID NO 1
<211> LENGTH: 500
<212> TYPE: PRT
<213> ORGANISM: Human papillomavirus type 6

<400> SEQUENCE: 1

Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255
```

```
Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser Gly Tyr Arg Gly Arg Ser Ser Ile Arg Thr Gly Val Lys
465                 470                 475                 480

Arg Pro Ala Val Ser Lys Ala Ser Ala Ala Pro Lys Arg Lys Arg Ala
                485                 490                 495

Lys Thr Lys Arg
            500


<210> SEQ ID NO 2
<211> LENGTH: 500
<212> TYPE: PRT
<213> ORGANISM: Artificial Sequence
<220> FEATURE:
<223> OTHER INFORMATION: Modified HPV6 L1

<400> SEQUENCE: 2

Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110
```

```
Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser Gly Tyr Gly Gly Arg Ser Ser Ile Ala Thr Gly Val Gly
465                 470                 475                 480

Ala Pro Ala Val Ser Gly Ala Ser Ala Ala Pro Ala Gly Ala Ala Ala
                485                 490                 495

Gly Thr Lys Arg
            500
```

<210> SEQ ID NO 3
<211> LENGTH: 500
<212> TYPE: PRT

<213> ORGANISM: Artificial Sequence
<220> FEATURE:
<223> OTHER INFORMATION: Modified HPV6 L1

<400> SEQUENCE: 3

```
Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
```

```
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser Gly Tyr Arg Gly Gly Ser Ser Ile Arg Thr Gly Val Gly
465                 470                 475                 480

Ser Pro Ala Val Ser Lys Ala Ser Ala Ala Pro Asp Gly Ser Gly Ala
                485                 490                 495

Gly Thr Lys Arg
            500


<210> SEQ ID NO 4
<211> LENGTH: 500
<212> TYPE: PRT
<213> ORGANISM: Artificial Sequence
<220> FEATURE:
<223> OTHER INFORMATION: Modified HPV6 L1

<400> SEQUENCE: 4

Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
```

```
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser Gly Tyr Arg Gly Gly Ser Ser Ile Arg Thr Gly Val Asp
465                 470                 475                 480

Gly Pro Ala Val Ser Lys Ala Ser Ala Ala Pro Asp Gly Ser Arg Ala
                485                 490                 495

Gly Thr Lys Arg
            500


<210> SEQ ID NO 5
<211> LENGTH: 500
<212> TYPE: PRT
<213> ORGANISM: Artificial Sequence
<220> FEATURE:
<223> OTHER INFORMATION: Modified HPV6 L1

<400> SEQUENCE: 5

Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
```

```
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser Gly Tyr Arg Gly Gly Ser Ser Ile Arg Thr Gly Val Gly
465                 470                 475                 480

Ser Pro Ala Val Ser Lys Ala Ser Ala Ala Pro Asp Gly Ser Arg Ala
                485                 490                 495

Asp Thr Lys Arg
            500
```

<210> SEQ ID NO 6

<211> LENGTH: 500
<212> TYPE: PRT
<213> ORGANISM: Artificial Sequence
<220> FEATURE:
<223> OTHER INFORMATION: Modified HPV6 L1

<400> SEQUENCE: 6

```
Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380
```

```
Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser Gly Tyr Arg Gly Gly Ser Ser Ile Arg Thr Gly Val Asp
465                 470                 475                 480

Gly Pro Ala Val Ser Lys Ala Ser Ala Ala Pro Asp Gly Ser Arg Ala
                485                 490                 495

Asp Thr Lys Arg
            500


<210> SEQ ID NO 7
<211> LENGTH: 500
<212> TYPE: PRT
<213> ORGANISM: Artificial Sequence
<220> FEATURE:
<223> OTHER INFORMATION: Modified HPV6 L1

<400> SEQUENCE: 7

Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240
```

```
Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser Gly Tyr Arg Gly Gly Ser Ser Ile Arg Thr Gly Val Gly
465                 470                 475                 480

Ser Pro Ala Val Ser Ser Ala Ser Ala Ala Pro Ser Gly Ser Gly Ala
                485                 490                 495

Gly Thr Gly Arg
            500
```

<210> SEQ ID NO 8
<211> LENGTH: 500
<212> TYPE: PRT
<213> ORGANISM: Artificial Sequence
<220> FEATURE:
<223> OTHER INFORMATION: Modified HPV6 L1

<400> SEQUENCE: 8

```
Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95
```

-continued

```
Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser Gly Tyr Arg Gly Gly Ser Ser Ile Ala Thr Gly Val Asp
465                 470                 475                 480

Gly Pro Ala Val Ser Lys Ala Ser Ala Ala Pro Ser Gly Ser Gly Ala
                485                 490                 495

Gly Thr Lys Arg
            500
```

```
<210> SEQ ID NO 9
<211> LENGTH: 500
<212> TYPE: PRT
<213> ORGANISM: Artificial Sequence
<220> FEATURE:
<223> OTHER INFORMATION: Modified HPV6 L1

<400> SEQUENCE: 9

Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365
```

```
Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser Gly Tyr Arg Gly Asp Ser Ser Ile Arg Thr Gly Val Asp
465                 470                 475                 480

Arg Pro Ala Val Ser Lys Ala Ser Ala Ala Pro Asp Ala Lys Ser Ala
                485                 490                 495

Lys Thr Gly Arg
            500


<210> SEQ ID NO 10
<211> LENGTH: 1504
<212> TYPE: DNA
<213> ORGANISM: Artificial Sequence
<220> FEATURE:
<223> OTHER INFORMATION: Modified HPV6 L1

<400> SEQUENCE: 10

atgtggcgtc cctcagattc aaccgtgtac gtcccccccc ctaatcccgt gtccaaagtc      60

gtcgctaccg acgcctacgt caccaggaca aatatcttct accacgcttc atccagccgc     120

ttgttggccg tcggccaccc ctacttcagc attaagcgcg ctaataagac cgtcgtgccc     180

aaagtcagcg gctaccagta ccgcgtcttc aaagtggtcc tccccgaccc caataaattc     240

gccctgcccg acagctccct cttcgatcct accacccaaa ggctggtgtg ggcctgtacc     300

ggcctcgaag tgggtcgcgg ccagcccctg ggtgtcggcg tctccggcca ccccttcttg     360

aataagtacg acgacgtgga gaactccggc tccggcggca accccggcca agacaaccgc     420

gtcaacgtgg gcatggacta caagcagaca caattgtgca tggtcggttg cgcccccccc     480

ctgggcgagc actggggcaa aggcaagcag tgcaccaaca cacctgtgca ggctggcgat     540

tgtcctcccc tcgagttgat cacatccgtc atccaagacg gcgatatggt cgacaccggt     600

ttcggcgcca tgaacttcgc cgatctgcag acaaacaaga gcgacgtccc tatcgacatc     660

tgcggcacca cctgtaagta ccccgactac ctccagatgg ccgccgatcc ctacggcgac     720

cgcctcttct tcttcctcag gaaagagcag atgttcgccc gccatttctt caaccgcgct     780

ggcgaggtcg gcgagcccgt ccccgacacc ctcatcatca agggctccgg taatcgcacc     840

agcgtgggct cctccatcta cgtgaacacc ccctccggta gcctcgtcag cagcgaagcc     900

cagctgttca acaagcccta ctggttgcag aaagcccaag gccacaataa cggcatctgt     960

tggggcaatc agctcttcgt caccgtcgtg gacacaacca ggtccaccaa catgaccttg    1020

tgcgccagcg tcaccaccag ctccacctac accaacagcg actacaaaga gtacatgagg    1080

cacgtcgaag aatacgacct gcaattcatc ttccagctct gctcaatcac cctgagcgcc    1140

gaggtgatgg cttacatcca taccatgaac cccagcgtcc tcgaagattg gaatttcggt    1200

ctgagccccc cccccaacgg caccctcgaa gacacctacc gctacgtgca aagccaagct    1260
```

atcacatgcc aaaagcctac ccccgagaag gagaagccag acccttacaa aaacctgtcc 1320
ttctgggaag tcaatctgaa ggagaaattc agctccgagc tggaccaata ccctttgggc 1380
aggaaattcc tgctccagtc cggctacgga ggccgatcca gcatcgcaac cggcgtggga 1440
gcacccgccg tcagcggagc tagcgccgct cctgcaggag ccgcagctgg gacaaagcgt 1500
taat 1504

<210> SEQ ID NO 11
<211> LENGTH: 1504
<212> TYPE: DNA
<213> ORGANISM: Artificial Sequence
<220> FEATURE:
<223> OTHER INFORMATION: Modified HPV6 L1

<400> SEQUENCE: 11
atgtggcgtc cctcagattc aaccgtgtac gtcccccccc ctaatcccgt gtccaaagtc 60
gtcgctaccg acgcctacgt caccaggaca aatatcttct accacgcttc atccagccgc 120
ttgttggccg tcggccaccc ctacttcagc attaagcgcg ctaataagac cgtcgtgccc 180
aaagtcagcg gctaccagta ccgcgtcttc aaagtggtcc tccccgaccc caataaattc 240
gccctgcccg acagctccct cttcgatcct accacccaaa ggctggtgtg ggcctgtacc 300
ggcctcgaag tgggtcgcgg ccagcccctg ggtgtcggcg tctccggcca ccccttcttg 360
aataagtacg acgacgtgga gaactccggc tccggcggca accccggcca agacaaccgc 420
gtcaacgtgg gcatggacta caagcagaca caattgtgca tggtcggttg cgcccccccc 480
ctgggcgagc actggggcaa aggcaagcag tgcaccaaca cacctgtgca ggctggcgat 540
tgtcctcccc tcgagttgat cacatccgtc atccaagacg gcgatatggt cgacaccggt 600
ttcggcgcca tgaacttcgc cgatctgcag acaaacaaga gcgacgtccc tatcgacatc 660
tgcggcacca cctgtaagta ccccgactac ctccagatgg ccgccgatcc ctacggcgac 720
cgcctcttct tcttcctcag gaaagagcag atgttcgccc gccatttctt caaccgcgct 780
ggcgaggtcg gcgagcccgt ccccgacacc ctcatcatca agggctccgg taatcgcacc 840
agcgtgggct cctccatcta cgtgaacacc ccctccggta gcctcgtcag cagcgaagcc 900
cagctgttca acaagcccta ctggttgcag aaagcccaag gccacaataa cggcatctgt 960
tggggcaatc agctcttcgt caccgtcgtg gacacaacca ggtccaccaa catgaccttg 1020
tgcgccagcg tcaccaccag ctccacctac accaacagcg actacaaaga gtacatgagg 1080
cacgtcgaag aatacgacct gcaattcatc ttccagctct gctcaatcac cctgagcgcc 1140
gaggtgatgg cttacatcca taccatgaac cccagcgtcc tcgaagattg gaatttcggt 1200
ctgagccccc cccccaacgg caccctcgaa gacacctacc gctacgtgca aagccaagct 1260
atcacatgcc aaaagcctac ccccgagaag gagaagccag acccttacaa aaacctgtcc 1320
ttctgggaag tcaatctgaa ggagaaattc agctccgagc tggaccaata ccctttgggc 1380
aggaaattcc tgctccagtc cggctaccga ggcggatcca gcatccgaac cggcgtggga 1440
agtcccgccg tcagcaaggc tagcgccgct cctgatggaa gcggagctgg gacaaagcgt 1500
taat 1504

<210> SEQ ID NO 12
<211> LENGTH: 1504
<212> TYPE: DNA
<213> ORGANISM: Artificial Sequence
<220> FEATURE:
<223> OTHER INFORMATION: Modified HPV6 L1

<400> SEQUENCE: 12

```
atgtggcgtc cctcagattc aaccgtgtac gtcccccccc ctaatcccgt gtccaaagtc     60
gtcgctaccg acgcctacgt caccaggaca aatatcttct accacgcttc atccagccgc    120
ttgttggccg tcggccaccc ctacttcagc attaagcgcg ctaataagac cgtcgtgccc    180
aaagtcagcg gctaccagta ccgcgtcttc aaagtggtcc tccccgaccc caataaattc    240
gccctgcccg acagctccct cttcgatcct accacccaaa ggctggtgtg ggcctgtacc    300
ggcctcgaag tgggtcgcgg ccagcccctg ggtgtcggcg tctccggcca ccccttcttg    360
aataagtacg acgacgtgga gaactccggc tccggcggca accccggcca agacaaccgc    420
gtcaacgtgg gcatggacta caagcagaca caattgtgca tggtcggttg cgcccccccc    480
ctgggcgagc actggggcaa aggcaagcag tgcaccaaca cacctgtgca ggctggcgat    540
tgtcctcccc tcgagttgat cacatccgtc atccaagacg gcgatatggt cgacaccggt    600
ttcggcgcca tgaacttcgc cgatctgcag acaaacaaga gcgacgtccc tatcgacatc    660
tgcggcacca cctgtaagta ccccgactac ctccagatgg ccgccgatcc ctacggcgac    720
cgcctcttct tcttcctcag gaaagagcag atgttcgccc gccatttctt caaccgcgct    780
ggcgaggtcg gcgagcccgt ccccgacacc ctcatcatca agggctccgg taatcgcacc    840
agcgtgggct cctccatcta cgtgaacacc ccctccggta gcctcgtcag cagcgaagcc    900
cagctgttca acaagcccta ctggttgcag aaagcccaag gccacaataa cggcatctgt    960
tggggcaatc agctcttcgt caccgtcgtg gacacaacca ggtccaccaa catgaccttg   1020
tgcgccagcg tcaccaccag ctccacctac accaacagcg actacaaaga gtacatgagg   1080
cacgtcgaag aatacgacct gcaattcatc ttccagctct gctcaatcac cctgagcgcc   1140
gaggtgatgg cttacatcca taccatgaac cccagcgtcc tcgaagattg gaatttcggt   1200
ctgagccccc cccccaacgg caccctcgaa gacacctacc gctacgtgca aagccaagct   1260
atcacatgcc aaaagcctac ccccgagaag gagaagccag acccttacaa aaacctgtcc   1320
ttctgggaag tcaatctgaa ggagaaattc agctccgagc tggaccaata ccctttgggc   1380
aggaaattcc tgctccagtc cggctaccga ggcggatcca gcatccgaac cggcgtggat   1440
ggacccgccg tcagcaaggc tagcgccgct cctgatggaa gcagagctgg gacaaagcgt   1500
taat                                                                1504
```

<210> SEQ ID NO 13
<211> LENGTH: 1504
<212> TYPE: DNA
<213> ORGANISM: Artificial Sequence
<220> FEATURE:
<223> OTHER INFORMATION: Modified HPV6 L1

<400> SEQUENCE: 13

```
atgtggcgtc cctcagattc aaccgtgtac gtcccccccc ctaatcccgt gtccaaagtc     60
gtcgctaccg acgcctacgt caccaggaca aatatcttct accacgcttc atccagccgc    120
ttgttggccg tcggccaccc ctacttcagc attaagcgcg ctaataagac cgtcgtgccc    180
aaagtcagcg gctaccagta ccgcgtcttc aaagtggtcc tccccgaccc caataaattc    240
gccctgcccg acagctccct cttcgatcct accacccaaa ggctggtgtg ggcctgtacc    300
ggcctcgaag tgggtcgcgg ccagcccctg ggtgtcggcg tctccggcca ccccttcttg    360
aataagtacg acgacgtgga gaactccggc tccggcggca accccggcca agacaaccgc    420
```

```
gtcaacgtgg gcatggacta caagcagaca caattgtgca tggtcggttg cgcccccccc    480
ctgggcgagc actggggcaa aggcaagcag tgcaccaaca cacctgtgca ggctggcgat    540
tgtcctcccc tcgagttgat cacatccgtc atccaagacg gcgatatggt cgacaccggt    600
ttcggcgcca tgaacttcgc cgatctgcag acaaacaaga gcgacgtccc tatcgacatc    660
tgcggcacca cctgtaagta ccccgactac ctccagatgg ccgccgatcc ctacggcgac    720
cgcctcttct tcttcctcag gaaagagcag atgttcgccc gccatttctt caaccgcgct    780
ggcgaggtcg gcgagcccgt ccccgacacc ctcatcatca agggctccgg taatcgcacc    840
agcgtgggct cctccatcta cgtgaacacc ccctccggta gcctcgtcag cagcgaagcc    900
cagctgttca acaagcccta ctggttgcag aaagcccaag gccacaataa cggcatctgt    960
tggggcaatc agctcttcgt caccgtcgtg gacacaacca ggtccaccaa catgaccttg   1020
tgcgccagcg tcaccaccag ctccacctac accaacagcg actacaaaga gtacatgagg   1080
cacgtcgaag aatacgacct gcaattcatc ttccagctct gctcaatcac cctgagcgcc   1140
gaggtgatgg cttacatcca taccatgaac cccagcgtcc tcgaagattg gaatttcggt   1200
ctgagccccc cccccaacgg caccctcgaa gacacctacc gctacgtgca aagccaagct   1260
atcacatgcc aaaagcctac ccccgagaag gagaagccag acccttacaa aaacctgtcc   1320
ttctgggaag tcaatctgaa ggagaaattc agctccgagc tggaccaata ccctttgggc   1380
aggaaattcc tgctccagtc cggctaccga ggcggatcca gcatccgaac cggcgtggga   1440
agtcccgccg tcagcaaggc tagcgccgct cctgatggaa gcagagctga tacaaagcgt   1500
taat                                                                1504
```

```
<210> SEQ ID NO 14
<211> LENGTH: 1504
<212> TYPE: DNA
<213> ORGANISM: Artificial Sequence
<220> FEATURE:
<223> OTHER INFORMATION: Modified HPV6 L1

<400> SEQUENCE: 14
```

```
atgtggcgtc cctcagattc aaccgtgtac gtcccccccc ctaatcccgt gtccaaagtc     60
gtcgctaccg acgcctacgt caccaggaca aatatcttct accacgcttc atccagccgc    120
ttgttggccg tcggccaccc ctacttcagc attaagcgcg ctaataagac cgtcgtgccc    180
aaagtcagcg gctaccagta ccgcgtcttc aaagtggtcc tccccgaccc caataaattc    240
gccctgcccg acagctccct cttcgatcct accacccaaa ggctggtgtg ggcctgtacc    300
ggcctcgaag tgggtcgcgg ccagcccctg ggtgtcggcg tctccggcca ccccttcttg    360
aataagtacg acgacgtgga gaactccggc tccggcggca accccggcca agacaaccgc    420
gtcaacgtgg gcatggacta caagcagaca caattgtgca tggtcggttg cgcccccccc    480
ctgggcgagc actggggcaa aggcaagcag tgcaccaaca cacctgtgca ggctggcgat    540
tgtcctcccc tcgagttgat cacatccgtc atccaagacg gcgatatggt cgacaccggt    600
ttcggcgcca tgaacttcgc cgatctgcag acaaacaaga gcgacgtccc tatcgacatc    660
tgcggcacca cctgtaagta ccccgactac ctccagatgg ccgccgatcc ctacggcgac    720
cgcctcttct tcttcctcag gaaagagcag atgttcgccc gccatttctt caaccgcgct    780
ggcgaggtcg gcgagcccgt ccccgacacc ctcatcatca agggctccgg taatcgcacc    840
agcgtgggct cctccatcta cgtgaacacc ccctccggta gcctcgtcag cagcgaagcc    900
cagctgttca acaagcccta ctggttgcag aaagcccaag gccacaataa cggcatctgt    960
```

```
tggggcaatc agctcttcgt caccgtcgtg gacacaacca ggtccaccaa catgaccttg   1020
tgcgccagcg tcaccaccag ctccacctac accaacagcg actacaaaga gtacatgagg   1080
cacgtcgaag aatacgacct gcaattcatc ttccagctct gctcaatcac cctgagcgcc   1140
gaggtgatgg cttacatcca taccatgaac cccagcgtcc tcgaagattg gaatttcggt   1200
ctgagccccc cccccaacgg caccctcgaa gacacctacc gctacgtgca aagccaagct   1260
atcacatgcc aaaagcctac ccccgagaag gagaagccag acccttacaa aaacctgtcc   1320
ttctgggaag tcaatctgaa ggagaaattc agctccgagc tggaccaata ccctttgggc   1380
aggaaattcc tgctccagtc cggctaccga ggcggatcca gcatccgaac cggcgtggat   1440
ggacccgccg tcagcaaggc tagcgccgct cctgatggaa gcagagctga tacaaagcgt   1500
taat                                                                1504
```

<210> SEQ ID NO 15
<211> LENGTH: 1504
<212> TYPE: DNA
<213> ORGANISM: Artificial Sequence
<220> FEATURE:
<223> OTHER INFORMATION: Modified HPV6 L1

<400> SEQUENCE: 15

```
atgtggcgtc cctcagattc aaccgtgtac gtcccccccc ctaatcccgt gtccaaagtc     60
gtcgctaccg acgcctacgt caccaggaca aatatcttct accacgcttc atccagccgc    120
ttgttggccg tcggccaccc ctacttcagc attaagcgcg ctaataagac cgtcgtgccc    180
aaagtcagcg gctaccagta ccgcgtcttc aaagtggtcc tccccgaccc caataaattc    240
gccctgcccg acagctccct cttcgatcct accacccaaa ggctggtgtg ggcctgtacc    300
ggcctcgaag tgggtcgcgg ccagcccctg ggtgtcggcg tctccggcca ccccttcttg    360
aataagtacg acgacgtgga gaactccggc tccggcggca accccggcca agacaaccgc    420
gtcaacgtgg gcatggacta caagcagaca caattgtgca tggtcggttg cgcccccccc    480
ctgggcgagc actggggcaa aggcaagcag tgcaccaaca cacctgtgca ggctggcgat    540
tgtcctcccc tcgagttgat cacatccgtc atccaagacg gcgatatggt cgacaccggt    600
ttcggcgcca tgaacttcgc cgatctgcag acaaacaaga gcgacgtccc tatcgacatc    660
tgcggcacca cctgtaagta ccccgactac ctccagatgg ccgccgatcc ctacggcgac    720
cgcctcttct tcttcctcag gaaagagcag atgttcgccc gccatttctt caaccgcgct    780
ggcgaggtcg gcgagcccgt ccccgacacc ctcatcatca agggctccgg taatcgcacc    840
agcgtgggct cctccatcta cgtgaacacc ccctccggta gcctcgtcag cagcgaagcc    900
cagctgttca acaagcccta ctggttgcag aaagcccaag gccacaataa cggcatctgt    960
tggggcaatc agctcttcgt caccgtcgtg gacacaacca ggtccaccaa catgaccttg   1020
tgcgccagcg tcaccaccag ctccacctac accaacagcg actacaaaga gtacatgagg   1080
cacgtcgaag aatacgacct gcaattcatc ttccagctct gctcaatcac cctgagcgcc   1140
gaggtgatgg cttacatcca taccatgaac cccagcgtcc tcgaagattg gaatttcggt   1200
ctgagccccc cccccaacgg caccctcgaa gacacctacc gctacgtgca aagccaagct   1260
atcacatgcc aaaagcctac ccccgagaag gagaagccag acccttacaa aaacctgtcc   1320
ttctgggaag tcaatctgaa ggagaaattc agctccgagc tggaccaata ccctttgggc   1380
aggaaattcc tgctccagtc cggctaccga ggcggatcca gcatccgaac cggcgtggga   1440
```

```
agtcccgccg tcagcagtgc tagcgccgct cctagtggaa gtggtgctgg gacaggacgt   1500

taat                                                                1504
```

<210> SEQ ID NO 16
<211> LENGTH: 1504
<212> TYPE: DNA
<213> ORGANISM: Artificial Sequence
<220> FEATURE:
<223> OTHER INFORMATION: Modified HPV6 L1

<400> SEQUENCE: 16

```
atgtggcgtc cctcagattc aaccgtgtac gtcccccccc ctaatcccgt gtccaaagtc     60

gtcgctaccg acgcctacgt caccaggaca aatatcttct accacgcttc atccagccgc    120

ttgttggccg tcggccaccc ctacttcagc attaagcgcg ctaataagac cgtcgtgccc    180

aaagtcagcg gctaccagta ccgcgtcttc aaagtggtcc tccccgaccc caataaattc    240

gccctgcccg acagctccct cttcgatcct accacccaaa ggctggtgtg ggcctgtacc    300

ggcctcgaag tgggtcgcgg ccagcccctg ggtgtcggcg tctccggcca ccccttcttg    360

aataagtacg acgacgtgga gaactccggc tccggcggca accccggcca agacaaccgc    420

gtcaacgtgg gcatggacta caagcagaca caattgtgca tggtcggttg cgcccccccc    480

ctgggcgagc actggggcaa aggcaagcag tgcaccaaca cacctgtgca ggctggcgat    540

tgtcctcccc tcgagttgat cacatccgtc atccaagacg gcgatatggt cgacaccggt    600

ttcggcgcca tgaacttcgc cgatctgcag acaaacaaga gcgacgtccc tatcgacatc    660

tgcggcacca cctgtaagta ccccgactac ctccagatgg ccgccgatcc ctacggcgac    720

cgcctcttct tcttcctcag gaaagagcag atgttcgccc gccatttctt caaccgcgct    780

ggcgaggtcg gcgagcccgt ccccgacacc ctcatcatca agggctccgg taatcgcacc    840

agcgtgggct cctccatcta cgtgaacacc ccctccggta gcctcgtcag cagcgaagcc    900

cagctgttca acaagcccta ctggttgcag aaagcccaag gccacaataa cggcatctgt    960

tggggcaatc agctcttcgt caccgtcgtg gacacaacca ggtccaccaa catgaccttg   1020

tgcgccagcg tcaccaccag ctccacctac accaacagcg actacaaaga gtacatgagg   1080

cacgtcgaag aatacgacct gcaattcatc ttccagctct gctcaatcac cctgagcgcc   1140

gaggtgatgg cttacatcca taccatgaac cccagcgtcc tcgaagattg gaatttcggt   1200

ctgagccccc cccccaacgg caccctcgaa gacacctacc gctacgtgca aagccaagct   1260

atcacatgcc aaaagcctac ccccgagaag gagaagccag acccttacaa aaacctgtcc   1320

ttctgggaag tcaatctgaa ggagaaattc agctccgagc tggaccaata ccctttgggc   1380

aggaaattcc tgctccagtc cggctaccga ggcggatcca gcatcgcaac cggcgtggat   1440

ggacccgccg tcagcaaggc tagcgccgct cctagtggaa gcggagctgg gacaaagcgt   1500

taat                                                                1504
```

<210> SEQ ID NO 17
<211> LENGTH: 1504
<212> TYPE: DNA
<213> ORGANISM: Artificial Sequence
<220> FEATURE:
<223> OTHER INFORMATION: Modified HPV6 L1

<400> SEQUENCE: 17

```
atgtggcgtc cctcagattc aaccgtgtac gtcccccccc ctaatcccgt gtccaaagtc     60

gtcgctaccg acgcctacgt caccaggaca aatatcttct accacgcttc atccagccgc    120
```

ttgttggccg tcggccaccc ctacttcagc attaagcgcg ctaataagac cgtcgtgccc 180
aaagtcagcg gctaccagta ccgcgtcttc aaagtggtcc tccccgaccc caataaattc 240
gccctgcccg acagctccct cttcgatcct accacccaaa ggctggtgtg ggcctgtacc 300
ggcctcgaag tgggtcgcgg ccagcccctg ggtgtcggcg tctccggcca ccccttcttg 360
aataagtacg acgacgtgga gaactccggc tccggcggca accccggcca agacaaccgc 420
gtcaacgtgg gcatggacta caagcagaca caattgtgca tggtcggttg cgcccccccc 480
ctgggcgagc actggggcaa aggcaagcag tgcaccaaca cacctgtgca ggctggcgat 540
tgtcctcccc tcgagttgat cacatccgtc atccaagacg gcgatatggt cgacaccggt 600
ttcggcgcca tgaacttcgc cgatctgcag acaaacaaga gcgacgtccc tatcgacatc 660
tgcggcacca cctgtaagta ccccgactac ctccagatgg ccgccgatcc ctacggcgac 720
cgcctcttct tcttcctcag gaaagagcag atgttcgccc gccatttctt caaccgcgct 780
ggcgaggtcg gcgagcccgt ccccgacacc ctcatcatca agggctccgg taatcgcacc 840
agcgtgggct cctccatcta cgtgaacacc ccctccggta gcctcgtcag cagcgaagcc 900
cagctgttca acaagcccta ctggttgcag aaagcccaag gccacaataa cggcatctgt 960
tggggcaatc agctcttcgt caccgtcgtg gacacaacca ggtccaccaa catgaccttg 1020
tgcgccagcg tcaccaccag ctccacctac accaacagcg actacaaaga gtacatgagg 1080
cacgtcgaag aatacgacct gcaattcatc ttccagctct gctcaatcac cctgagcgcc 1140
gaggtgatgg cttacatcca taccatgaac cccagcgtcc tcgaagattg gaatttcggt 1200
ctgagccccc cccccaacgg caccctcgaa gacacctacc gctacgtgca aagccaagct 1260
atcacatgcc aaaagcctac ccccgagaag gagaagccag acccttacaa aaacctgtcc 1320
ttctgggaag tcaatctgaa ggagaaattc agctccgagc tggaccaata ccctttgggc 1380
aggaaattcc tgctccagtc cggctaccga ggcgactcca gcatccgaac cggcgtggat 1440
cgacccgccg tcagcaaggc tagcgccgct cctgatgcaa agagtgctaa gacaggacgt 1500
taat 1504

<210> SEQ ID NO 18
<211> LENGTH: 1504
<212> TYPE: DNA
<213> ORGANISM: Human papillomavirus type 6

<400> SEQUENCE: 18
atgtggcgtc cctcagattc aaccgtgtac gtcccccccc ctaatcccgt gtccaaagtc 60
gtcgctaccg acgcctacgt caccaggaca aatatcttct accacgcttc atccagccgc 120
ttgttggccg tcggccaccc ctacttcagc attaagcgcg ctaataagac cgtcgtgccc 180
aaagtcagcg gctaccagta ccgcgtcttc aaagtggtcc tccccgaccc caataaattc 240
gccctgcccg acagctccct cttcgatcct accacccaaa ggctggtgtg ggcctgtacc 300
ggcctcgaag tgggtcgcgg ccagcccctg ggtgtcggcg tctccggcca ccccttcttg 360
aataagtacg acgacgtgga gaactccggc tccggcggca accccggcca agacaaccgc 420
gtcaacgtgg gcatggacta caagcagaca caattgtgca tggtcggttg cgcccccccc 480
ctgggcgagc actggggcaa aggcaagcag tgcaccaaca cacctgtgca ggctggcgat 540
tgtcctcccc tcgagttgat cacatccgtc atccaagacg gcgatatggt cgacaccggt 600
ttcggcgcca tgaacttcgc cgatctgcag acaaacaaga gcgacgtccc tatcgacatc 660

```
tgcggcacca cctgtaagta ccccgactac ctccagatgg ccgccgatcc ctacggcgac    720

cgcctcttct tcttcctcag gaaagagcag atgttcgccc gccatttctt caaccgcgct    780

ggcgaggtcg gcgagcccgt ccccgacacc ctcatcatca agggctccgg taatcgcacc    840

agcgtgggct cctccatcta cgtgaacacc ccctccggta gcctcgtcag cagcgaagcc    900

cagctgttca acaagcccta ctggttgcag aaagcccaag gccacaataa cggcatctgt    960

tggggcaatc agctcttcgt caccgtcgtg gacacaacca ggtccaccaa catgaccttg   1020

tgcgccagcg tcaccaccag ctccacctac accaacagcg actacaaaga gtacatgagg   1080

cacgtcgaag aatacgacct gcaattcatc ttccagctct gctcaatcac cctgagcgcc   1140

gaggtgatgg cttacatcca taccatgaac cccagcgtcc tcgaagattg gaatttcggt   1200

ctgagccccc cccccaacgg caccctcgaa gacacctacc gctacgtgca aagccaagct   1260

atcacatgcc aaaagcctac ccccgagaag gagaagccag acccttacaa aaacctgtcc   1320

ttctgggaag tcaatctgaa ggagaaattc agctccgagc tggaccaata ccctttgggc   1380

aggaaattcc tgctccagtc cggctacagg ggccgatcca gcatcaggac cggcgtgaaa   1440

aggcccgccg tcagcaaagc tagcgccgct cctaagagga agagggctaa gacaaagcgt   1500

taat                                                                1504
```

```
<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19

ggaattcgcc gccaccatgt g                                               21
```

```
<210> SEQ ID NO 20
<211> LENGTH: 59
<212> TYPE: DNA
<213> ORGANISM: Artificial Sequence
<220> FEATURE:
<223> OTHER INFORMATION: Primer

<400> SEQUENCE: 20

cccacgccgg ttgcgatgct ggatcggcct ccgtagccgg actggagcag gaatttcct      59
```

```
<210> SEQ ID NO 21
<211> LENGTH: 59
<212> TYPE: DNA
<213> ORGANISM: Artificial Sequence
<220> FEATURE:
<223> OTHER INFORMATION: Primer

<400> SEQUENCE: 21

gcaggagcgg cgctagctcc gctgacggcg ggtgctccca cgccggttgc gatgctgga      59
```

```
<210> SEQ ID NO 22
<211> LENGTH: 59
<212> TYPE: DNA
<213> ORGANISM: Artificial Sequence
<220> FEATURE:
<223> OTHER INFORMATION: Primer

<400> SEQUENCE: 22

gctctagaat taacgctttg tcccagctgc ggctcctgca ggagcggcgc tagctccgc      59
```

<210> SEQ ID NO 23
<211> LENGTH: 42
<212> TYPE: DNA
<213> ORGANISM: Artificial Sequence
<220> FEATURE:
<223> OTHER INFORMATION: Primer

<400> SEQUENCE: 23
cacgccggtt cggatgctgg atccgcctcg gtagccggac tg 42

<210> SEQ ID NO 24
<211> LENGTH: 54
<212> TYPE: DNA
<213> ORGANISM: Artificial Sequence
<220> FEATURE:
<223> OTHER INFORMATION: Primer

<400> SEQUENCE: 24
aggagcggcg ctagccttgc tgacggcggg acttcccacg ccggttcgga tgct 54

<210> SEQ ID NO 25
<211> LENGTH: 59
<212> TYPE: DNA
<213> ORGANISM: Artificial Sequence
<220> FEATURE:
<223> OTHER INFORMATION: Primer

<400> SEQUENCE: 25
gctctagaat taacgctttg tcccagctcc gcttccatca ggagcggcgc tagccttgc 59

<210> SEQ ID NO 26
<211> LENGTH: 42
<212> TYPE: DNA
<213> ORGANISM: Artificial Sequence
<220> FEATURE:
<223> OTHER INFORMATION: Primer

<400> SEQUENCE: 26
cacgccggtt cggatgctgg atccgcctcg gtagccggac tg 42

<210> SEQ ID NO 27
<211> LENGTH: 54
<212> TYPE: DNA
<213> ORGANISM: Artificial Sequence
<220> FEATURE:
<223> OTHER INFORMATION: Primer

<400> SEQUENCE: 27
aggagcggcg ctagccttgc tgacggcggg tccatccacg ccggttcgga tgct 54

<210> SEQ ID NO 28
<211> LENGTH: 59
<212> TYPE: DNA
<213> ORGANISM: Artificial Sequence
<220> FEATURE:
<223> OTHER INFORMATION: Primer

<400> SEQUENCE: 28
gctctagaat taacgctttg tcccagctct gcttccatca ggagcggcgc tagccttgc 59

<210> SEQ ID NO 29
<211> LENGTH: 42
<212> TYPE: DNA
<213> ORGANISM: Artificial Sequence
<220> FEATURE:
<223> OTHER INFORMATION: Primer

<400> SEQUENCE: 29
cacgccggtt cggatgctgg atccgcctcg gtagccggac tg 42

<210> SEQ ID NO 30
<211> LENGTH: 54
<212> TYPE: DNA
<213> ORGANISM: Artificial Sequence
<220> FEATURE:
<223> OTHER INFORMATION: Primer

<400> SEQUENCE: 30
aggagcggcg ctagccttgc tgacggcggg acttcccacg ccggttcgga tgct 54

<210> SEQ ID NO 31
<211> LENGTH: 59
<212> TYPE: DNA
<213> ORGANISM: Artificial Sequence
<220> FEATURE:
<223> OTHER INFORMATION: Primer

<400> SEQUENCE: 31
gctctagaat taacgctttg tatcagctct gcttccatca ggagcggcgc tagccttgc 59

<210> SEQ ID NO 32
<211> LENGTH: 42
<212> TYPE: DNA
<213> ORGANISM: Artificial Sequence
<220> FEATURE:
<223> OTHER INFORMATION: Primer

<400> SEQUENCE: 32
cacgccggtt cggatgctgg atccgcctcg gtagccggac tg 42

<210> SEQ ID NO 33
<211> LENGTH: 54
<212> TYPE: DNA
<213> ORGANISM: Artificial Sequence
<220> FEATURE:
<223> OTHER INFORMATION: Primer

<400> SEQUENCE: 33
aggagcggcg ctagccttgc tgacggcggg tccatccacg ccggttcgga tgct 54

<210> SEQ ID NO 34
<211> LENGTH: 59
<212> TYPE: DNA
<213> ORGANISM: Artificial Sequence
<220> FEATURE:
<223> OTHER INFORMATION: Primer

<400> SEQUENCE: 34
gctctagaat taacgctttg tatcagctct gcttccatca ggagcggcgc tagccttgc 59

<210> SEQ ID NO 35
<211> LENGTH: 42
<212> TYPE: DNA
<213> ORGANISM: Artificial Sequence
<220> FEATURE:
<223> OTHER INFORMATION: Primer

<400> SEQUENCE: 35
cacgccggtt cggatgctgg atccgcctcg gtagccggac tg 42

<210> SEQ ID NO 36
<211> LENGTH: 54

<212> TYPE: DNA
<213> ORGANISM: Artificial Sequence
<220> FEATURE:
<223> OTHER INFORMATION: Primer

<400> SEQUENCE: 36
aggagcggcg ctagcactgc tgacggcggg acttcccacg ccggttcgga tgct 54

<210> SEQ ID NO 37
<211> LENGTH: 59
<212> TYPE: DNA
<213> ORGANISM: Artificial Sequence
<220> FEATURE:
<223> OTHER INFORMATION: Primer

<400> SEQUENCE: 37
gctctagaat taacgtcctg tcccagcacc acttccacta ggagcggcgc tagcactgc 59

<210> SEQ ID NO 38
<211> LENGTH: 42
<212> TYPE: DNA
<213> ORGANISM: Artificial Sequence
<220> FEATURE:
<223> OTHER INFORMATION: Primer

<400> SEQUENCE: 38
cacgccggtt gcgatgctgg atccgcctcg gtagccggac tg 42

<210> SEQ ID NO 39
<211> LENGTH: 54
<212> TYPE: DNA
<213> ORGANISM: Artificial Sequence
<220> FEATURE:
<223> OTHER INFORMATION: Primer

<400> SEQUENCE: 39
aggagcggcg ctagccttgc tgacggcggg tccatccacg ccggttgcga tgct 54

<210> SEQ ID NO 40
<211> LENGTH: 59
<212> TYPE: DNA
<213> ORGANISM: Artificial Sequence
<220> FEATURE:
<223> OTHER INFORMATION: Primer

<400> SEQUENCE: 40
gctctagaat taacgctttg tcccagctcc gcttccacta ggagcggcgc tagccttgc 59

<210> SEQ ID NO 41
<211> LENGTH: 42
<212> TYPE: DNA
<213> ORGANISM: Artificial Sequence
<220> FEATURE:
<223> OTHER INFORMATION: Primer

<400> SEQUENCE: 41
cacgccggtt cggatgctgg agtcgcctcg gtagccggac tg 42

<210> SEQ ID NO 42
<211> LENGTH: 54
<212> TYPE: DNA
<213> ORGANISM: Artificial Sequence
<220> FEATURE:
<223> OTHER INFORMATION: Primer

<400> SEQUENCE: 42

-continued

```
aggagcggcg ctagccttgc tgacggcggg tcgatccacg ccggttcgga tgct          54


<210> SEQ ID NO 43
<211> LENGTH: 59
<212> TYPE: DNA
<213> ORGANISM: Artificial Sequence
<220> FEATURE:
<223> OTHER INFORMATION: Primer

<400> SEQUENCE: 43

gctctagaat taacgtcctg tcttagcact ctttgcatca ggagcggcgc tagccttgc      59
```

C-TERMINUS MODIFIED HUMAN PAPILLOMA VIRUS TYPE 6 L1 PROTEIN AND USE THEREOF

CROSS REFERENCE TO RELATED APPLICATIONS

The present application is the U.S. National Stage of International Application No. PCT/CN2021/120516, filed on Sep. 26, 2021, which claims the priority of Chinese Patent Application No. 202011347629.5, filed on Nov. 26, 2020, the contents of each of which are incorporated herein by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 60,599 byte ASCII (text) file named "Seq_List" created on Sep. 26, 2021.

FIELD OF THE INVENTION

The present application relates to the field of biotechnology. Specifically, the present application relates to a modified human papillomavirus protein, and a pentamer or a virus-like particle formed thereby, as well as use of the human papillomavirus protein, the pentamer or the human papillomavirus virus-like particle in the preparation of a vaccine for the prevention of papillomavirus infection and infection-induced diseases.

BACKGROUND OF THE INVENTION

Human papillomavirus (HPV) is a class of non-enveloped small DNA viruses that infect epithelial tissue. The viral genome is a double-stranded closed circular DNA of about 7.2-7.9 kb in size, with 8 open reading frames encoding a total of 6 early stage genes, E1, E2, E4, E5, E6 and E7, and a total of 2 late stage genes, L1 and L2, respectively. In addition, the genome also contains a long regulatory region. The viral particle has a diameter of about 45-44 nm. The shell is a regular icosahedron of T=7 composed of 72 L1 pentamers and 72 L2 proteins.

At present, more than 200 types of HPV have been identified, among which more than 40 types mainly infect the perianal, urogenital and oropharyngeal mucous membrane and adjacent skin. According to the nature of infection-induced lesions, they are classified into carcinogenic types that induce malignant tumors (HPV16, -18, -31, -33, -45, -52, -58, etc.) and low-risk types that induce verrucous hyperplasia (HPV6, -11, etc.). At present, there are about 20 types of carcinogenic HPV, among which 12 common carcinogenic types are high-risk types. Molecular epidemiological studies have found that persistent infection with carcinogenic HPV can induce about 100% of cervical cancer, 88% of anal cancer, 70% of vaginal cancer, 50% of penile cancer, 43% of vulva cancer, and 72% of head and neck cancer. At present, 12 types of low-risk HPV have been identified, namely HPV6, -7, -11, -13, -32, -40, -42, -43, -44, -54, -74 and -91. Among them, HPV6 and HPV11 types are the main prevalent types responsible for perianal, genital and pharyngeal mucosal warts worldwide. Analysis of HPV in a total of 10,757 condyloma accuminatum (CA) patients, from 67 literatures published in China during January 1990 to December 2013, found that the positive rate of HPV infection in CA patients was 86.7% (9328). The positive rate was 81.2% (3671/4623) for HPV6 and/or HPV11, 43.8% (2445/6134) for HPV6, 38.3% (2155/6134) for HPV11, and 21.7% (870/3781) for HPV16, HPV18 and/or HPV11. Analysis of HPV in 261 patients with genital warts (GW) diagnosed by biopsy histology in Colombia area, including 155 females and 106 males, showed that the detection rate of HPV was 87.7% in female and 90.6% in male GW patients. Among them, the detection rate of HPV6 was the highest, reaching 59.7% (155.8/261), 62% in females and 56% in males, respectively. The detection rate of HPV11 was the second highest, which was 29.8% (77.8/261). The detection rate of HPV16 ranked third, which was 16%. The total positive rate of HPV6 and HPV11 infection was 80.3%.

The L1 protein can be assembled into VLP after in vitro expression. The expression systems are mainly yeast expression systems, insect cell expression systems, *E. coli* expression systems, etc. The advantages of producing L1VLP vaccines using insect cell expression systems are high expression levels of soluble protein, easy cell disruption, and absence of endotoxin. The three L1VLP vaccines currently on the market are the Gardasil™ tetravalent vaccine (HPV16/18/6/11 L1VLP, aluminum phosphate sulfate adjuvant) and the Gardasil-9™ nine-valent vaccine (HPV16/18/6/11/31/33/45/52/58 L1VLP, aluminium phosphate sulfate adjuvant) produced by Merck using yeast expression systems, and the Cervarix™ bivalent vaccine (HPV16/18 L1VLP, AS04 adjuvant) produced by GSK using insect cell expression systems.

Clinical studies found that the titer of HPV16 and HPV18-specific neutralizing antibodies, The cell response and memory B cell number induced by a relatively low dose of 16L1VLP (20 μg/dose) and the same dose of 18L1VLP (20 μg/dose) of Cervarix™ were higher than those induced by Gardasil™ (40 μg of 16L1VLP and 20 μg of 18L1VLP in a single dose of Gardasil Gardasil™).

Increasing the expression level of HPV L1VLP in insect cells can significantly improve the purification yield of L1VLP and reduce the production cost of the vaccine. In prokaryotic expression systems, L1 of HPV16, -18, -31, -33, -45, -52, -58, -6, and -11 types was modified by N-terminus truncation, and it was found that the number of amino acids truncated at N-terminus that could upregulate the L1 expression level varies from type to type, and was irregular. In insect expression systems, BPV1 L1 was modified by C-terminus truncation, and it was found that the assembly efficiency of truncated BPV L1 increased by 3 folds. Although the VLP of HPV58 truncated L1 has been reported, the effect of C-terminus truncation on protein expression has not been reported. When using yeast expression systems, type 6 L1VLP was produced using codon-optimized full-length gene.

It has been found in the present application that C-terminus modification of L1 can significantly increase the expression level and yield of 6L1VLP, and the obtained HPV6 L1VLP can induce high titers of type-specific neutralizing antibodies.

SUMMARY OF THE INVENTION

The present application provides a novel C-terminus modified HPV6 L1 protein, a pentamer or a virus-like particle composed thereof, and a vaccine containing the pentamer or virus-like particle, and studies use of the vaccine in the prevention of HPV infection and infection-related diseases.

The inventor has unexpectedly found that appropriate substitution of C-terminus basic amino acids of HPV6 L1 protein can increase the expression amount of HPV6 L1 protein in insect cell expression systems. The truncated protein can be assembled into VLP and can induce a protective immune response against HPV6.

Thus, according to some embodiments of the present application, the present application relates to a HPV6 L1 protein, wherein one or more of the 31 basic amino acids at C-terminus were substituted with polar uncharged amino acids, non-polar amino acids and/or acidic amino acids, compared with wild-type HPV6 L1 protein.

Specifically, the present application provides a C-terminus modified HPV6 L1 protein, wherein one or more arginine (R) and/or lysine (K) within the 31 C-terminus amino acids of the modified HPV6 L1 protein are substituted with polar uncharged amino acids, non-polar amino acids and/or acidic amino acids, compared with wild-type HPV6 L1 protein. Preferably, the polar uncharged amino acid is selected from the group consisting of glycine (G), serine (S) and threonine (T), the non-polar amino acid is selected from the group consisting of alanine (A) and valine (V), and the acidic amino acid is aspartate (D) or glutamate (E).

In particular embodiments, the C-terminus modified HPV6 L1 protein of the present application is modified on the basis of the sequence as shown in SEQ ID No. 1 particularly preferably, the C-terminus modified HPV6 L1 protein is selected from the group consisting of 6L1CS1, 6L1CS2, 6L1CS3, 6L1CS4, 6L1CS5, 6L1CS6, 6L1CS7 and 6L1CS8, the amino acid sequences of which are as shown in SEQ ID No. 2, SEQ ID No. 3, SEQ ID No. 4, SEQ ID No. 5, SEQ ID No. 6, SEQ ID No. 7, SEQ ID No. 8 and SEQ ID No. 9, respectively.

According to some embodiments of the present application, the present application relates to a polynucleotide encoding the C-terminus modified HPV6 L1 protein of the present application. Preferably, the polynucleotide is optimized using codons of commonly used expression systems, such as *E. coli* expression systems, yeast expression systems, insect cell expression systems, etc. Preferably, the polynucleotide is optimized using insect cell codons.

According to some embodiments of the present application, the present application relates to a vector containing the above-mentioned polynucleotide. Preferably, the vector is selected from the group consisting of plasmid, recombinant Bacmid and recombinant baculovirus.

According to some embodiments of the present application, the present application relates to a cell comprising the above-mentioned vector. Preferably, the cell is an *E. coli* cell, a yeast cell or an insect cell, and particularly preferably, the cell is an insect cell.

According to some embodiments of the present application, the present application relates to a HPV6 L1 multimer or a virus-like particle, the multimer (e.g., pentamer) or virus-like particle contains the above-mentioned C-terminus modified HPV6 L1 protein or is composed of the same.

According to some embodiments of the present application, the present application relates to a vaccine for the prevention of HPV infection or HPV infection-related diseases comprising the above-mentioned HPV6 L1 multimer or virus-like particle, wherein the content of the HPV6 L1 virus-like particle is an effective amount that can induce a protective immune response. Preferably, the vaccine can also comprise at least one selected from other mucosa-tropic and/or skin-tropic HPV pentamer or virus-like particle, the content of which is an effective amount that can induce a protective immune response, respectively. The above-mentioned vaccine usually also comprises an excipient or carrier for vaccines.

Preferably, the vaccine contains the above-mentioned HPV6 L1 multimer or virus-like particle, as well as at least one selected from the group consisting of HPV2, -5, -7, -8, -11, -16, -18, -26, -27, -28, -29, -30, -31, -32, -33, -34, -35, -38, -39, -40, -43, -44, -45, -51, -52, -53, -56, -57, -58, -59, -61, -66, -67, -68, -69, -70, -73, -74, -77, -81, -82, -83, -85, -91 L1 virus-like particles, the content of which is an effective amount that can induce a protective immune response, respectively.

Further preferably, the vaccine contains the above-mentioned HPV6 L1 multimer or virus-like particle, as well as HPV11, -16, -18, -26, -31, -33, -35, -39, -45, -51, -52, -56, -58, -59, -68 and -73 L1 virus-like particles, the content of which is an effective amount that can induce a protective immune response, respectively.

Further preferably, the vaccine contains the above-mentioned HPV6 L1 multimer or virus-like particle, as well as HPV11, -16, -18, -31, -33, -35, -39, -45, -52 and -58 L1 virus-like particles, the content of which is an effective amount that can induce a protective immune response, respectively.

Further preferably, the vaccine contains the above-mentioned HPV6 L1 multimer or virus-like particle, as well as HPV11, -16, -18, -52 and -58 L1 virus-like particles, the content of which is an effective amount that can induce a protective immune response, respectively.

Further preferably, the vaccine contains the above-mentioned HPV6 L1 multimer or virus-like particle, as well as HPV16, -18 and -58 L1 virus-like particles, the content of which is an effective amount that can induce a protective immune response, respectively.

Particularly preferably, the vaccine contains the above-mentioned HPV6 L1 multimer or virus-like particle, as well as HPV11 L1 virus-like particle, the content of which is an effective amount that can induce a protective immune response, respectively.

According to some embodiments of the present application, the present application relates to a novel vaccine comprising the above-mentioned HPV6 L1 multimer or virus-like particle as well as an adjuvant, which can further enhance the immune response. Preferably, the adjuvant used is a vaccine adjuvant for human use.

According to some embodiments of the present application, the present application relates to use of the above-mentioned vaccine in the prevention of HPV infection or HPV infection-related diseases.

DESCRIPTION AND EXPLANATION OF RELEVANT TERMS

According to the present application, the term "insect cell expression system" includes insect cell, recombinant baculovirus, recombinant Bacmid and expression vector. Among them, the insect cell is derived from a commercially available cell, the examples of which are listed here but not limited to: Sf9, Sf21, High Five.

According to the present application, the term "excipient or carrier" refers to that selected from one or more of the following, including but not limited to, pH adjuster, surfactant and ionic strength enhancer. For example, the pH adjuster is for example but not limited to phosphate buffer. The surfactant includes cationic, anionic or nonionic surfactant, and is for example but not limited to polysorbate 80. The ionic strength enhancer is for example but not limited to sodium chloride.

According to the present application, the term "adjuvant" refers to an adjuvant that can be applied clinically to the human body, including various adjuvants that have been approved and may be approved in the future.

According to the present application, the vaccine of the present application can be in a patient-acceptable form, including but not limited to oral administration or injection, preferably injection.

According to the present application, the vaccine of the present application is preferably used in a unit dosage form, wherein the dose of the C-terminus modified HPV6 L1 protein virus-like particle in the unit dosage form is 5 μg-80 μg, preferably 20 μg-40 μg.

DESCRIPTION OF THE DRAWINGS

FIG. 2A represents wild-type HPV6L1, FIG. 2B represents 6L1CS4, and FIG. 2C represents 6L1CS6.

FIG. 3A and FIG. 3B represent 6L1CS4 and 6L1CS6, respectively.

DETAILED DESCRIPTION OF THE INVENTION

Figure 1:
FIG. 1 shows the expression and identification of the C-terminus modified HPV6 L1 in Example 4 of the present application in insect cells. The results show that all eight 40 types of C-terminus modified HPV6 L1 can be expressed at high levels in insect cells. Lanes 1 to 9 represent 6L1 (wild-type), 6L1CS1, 6L1CS2, 6L1CS3, 6L1CS4, 6L1CS5, 6L1CS6, 6L1CS7 and 6L1CS8, respectively.

The present application will be further illustrated by the non-limiting examples below. It is well known to those skilled in the art that many modifications can be made to the present application without departing from the spirit of the present application, and such modifications also fall within the scope of the present application. The following embodiments are only used to illustrate the present application and should not be regarded as limiting the scope of the present application, as the embodiments are necessarily diverse. The terms used in the present specification are intended only to describe particular embodiments but not as limitations. The scope of the present application has been defined in the appended claims.

Unless otherwise specified, all the technical and scientific terms used in the present specification have the same meaning as those generally understood by those skilled in the technical field to which the present application relates. Preferred methods and materials of the present application are described below, but any method and material similar or equivalent to the methods and materials described in the present specification can be used to implement or test the present application. Unless otherwise specified, the following experimental methods are conventional methods or methods described in product specifications. Unless otherwise specified, the experimental materials used are easily available from commercial companies.

Example 1: Amplification of C-Terminus Modified HPV6L1 Gene and Construction of Expression Vectors The full-length HPV6L1 gene (as shown in SEQ ID No. 18) used as the template was whole-gene synthesized by Shanghai Sangon Biotech Co., Ltd., and its corresponding amino acid sequence was the sequence as shown in SEQ ID No. 1.

The primers used to construct the C-terminus modified HPV6L1 gene were synthesized by Shanghai Sangon Biotech Co., Ltd.

1) 6L1CS1 gene: SEQ ID No. 18 was used as the template and 6L1F/6L1CS1R1 as primers for PCR amplification to obtain 6L1CS1-1 intermediate product. Then the 6L1CS1-1 intermediate product was used as the template and 6L1F/6L1CS1R2 as primers for PCR amplification to obtain 6L1CS1-2 intermediate product. Finally, the 6L1CS1-2 intermediate product was used as the template and 6L1F/6L1CS1R3 as primers for PCR amplification to obtain 6L1CS1 gene, the sequence of which was as shown in SEQ ID No. 10;
2) 6L1CS2 gene: SEQ ID No. 18 was used as the template and 6L1F/6L1CS2R1 as primers for PCR amplification to obtain 6L1CS2-1 intermediate product. Then the 6L1CS2-1 intermediate product was used as the template and 6L1F/6L1CS2R2 as primers for PCR amplification to obtain 6L1CS2-2 intermediate product. Finally, the 6L1CS2-2 intermediate product was used as the template and 6L1F/6L1CS2R3 as primers for PCR amplification to obtain 6L1CS2 gene, the sequence of which was as shown in SEQ ID No. 11;
3) 6L1CS3 gene: SEQ ID No. 18 was used as the template and 6L1F/6L1CS3R1 as primers for PCR amplification to obtain 6L1CS3-1 intermediate product. Then the 6L1CS3-1 intermediate product was used as the template and 6L1F/6L1CS3R2 as primers for PCR amplification to obtain 6L1CS3-2 intermediate product. Finally, the 6L1CS3-2 intermediate product was used as the template and 6L1F/6L1CS3R3 as primers for PCR amplification to obtain 6L1CS3 gene, the sequence of which was as shown in SEQ ID No. 12;
4) 6L1CS4 gene: SEQ ID No. 18 was used as the template and 6L1F/6L1CS4R1 as primers for PCR amplification to obtain 6L1CS4-1 intermediate product. Then the 6L1CS4-1 intermediate product was used as the template and 6L1F/6L1CS4R2 as primers for PCR amplification to obtain 6L1CS4-2 intermediate product. Finally, the 6L1CS4-2 intermediate product was used as the template and 6L1F/6L1CS4R3 as primers for PCR amplification to obtain 6L1CS4 gene, the sequence of which was as shown in SEQ ID No. 13;
5) 6L1CS5 gene: SEQ ID No. 18 was used as the template and 6L1F/6L1CS5R1 as primers for PCR amplification to obtain 6L1CS5-1 intermediate product. Then the 6L1CS5-1 intermediate product was used as the template and 6L1F/6L1CS5R2 as primers for PCR amplification to obtain 6L1CS5-2 intermediate product. Finally, the 6L1CS5-2 intermediate product was used as the template and 6L1F/6L1CS5R3 as primers for PCR amplification to obtain 6L1CS5 gene, the sequence of which was as shown in SEQ ID No. 14;

6) 6L1CS6 gene: SEQ ID No. 18 was used as the template and 6L1F/6L1CS6R1 as primers for PCR amplification to obtain 6L1CS6-1 intermediate product. Then the 6L1CS6-1 intermediate product was used as the template and 6L1F/6L1CS6R2 as primers for PCR amplification to obtain 6L1CS6-2 intermediate product. Finally, the 6L1CS6-2 intermediate product was used as the template and 6L1F/6L1CS6R3 as primers for PCR amplification to obtain 6L1CS6 gene, the sequence of which was as shown in SEQ ID No. 15;

7) 6L1CS7 gene: SEQ ID No. 18 was used as the template and 6L1F/6L1CS7R1 as primers for PCR amplification to obtain 6L1CS7-1 intermediate product. Then the 6L1CS7-1 intermediate product was used as the template and 6L1F/6L1CS7R2 as primers for PCR amplification to obtain 6L1CS7-2 intermediate product. Finally, the 6L1CS7-2 intermediate product was used as the template and 6L1F/6L1CS7R3 as primers for PCR amplification to obtain 6L1CS7 gene, the sequence of which was as shown in SEQ ID No. 16;

8) 6L1CS8 gene: SEQ ID No. 18 was used as the template and 6L1F/6L1CS8R1 as primers for PCR amplification to obtain 6L1CS8-1 intermediate product. Then the 6L1CS8-1 intermediate product was used as the template and 6L1F/6L1CS8R2 as primers for PCR amplification to obtain 6L1CS8-2 intermediate product. Finally, the 6L1CS8-2 intermediate product was used as the template and 6L1F/6L1CS8R3 as primers for PCR amplification to obtain 6L1CS8 gene, the sequence of which was as shown in SEQ ID No. 16.

The EcoRI/XbaI restriction sites were used to digest the above-mentioned PCR-amplified genes respectively, which were inserted into the commercial expression vector pFastBac1™ (produced by Invitrogen) respectively to obtain recombinant expression vectors comprising the C-terminus modified HPV6L1 genes, pFastBac1-6L1CS1™, pFastBac1-6L1CS2™, pFastBac1-6L1CS3™, pFastBac1-6L1CS4™, pFastBac1-6L1CS5™. pFastBac1-6L1CS6™, pFastBac1-6L1CS7™ and pFastBac1-6L1CS8™. The above-mentioned methods of enzyme digestion, ligation and construction of clones were all well known.

Example 2: Recombinant Bacmid and Recombinant Baculovirus Constructs of the C-Terminus Modified HPV6L1 Gene The recombinant expression vectors comprising the C-terminus modified HPV6L1 gene, pFastBac1-6L1CS1™, pFastBac1-6L1CS2™, pFastBac1-6L1CS3™, pFastBac1-6L1CS4™, pFastBac1-6L1CS5™, pFastBac1-6L1CS6™, pFastBac1-6L1CS7™ and pFastBac1-6L1CS8™, were used to transform *E. coli* DH10Bac competent cells respectively. Screening was performed to obtain recombinant Bacmids, which were then used to transfect Sf9 insect cells to amplify recombinant baculoviruses within Sf9. Methods for screening of recombinant Bacmid and amplification of recombinant baculovirus were all well known.

Example 3: Expression of C-Terminus Modified HPV6L1 Gene in Sf9 Cells

Sf9 cells were inoculated with the recombinant baculovirus carrying optimized wild-type HPV6L1 gene and the 8 C-terminus modified HPV6L1 genes to express the C-terminus modified HPV6L1 proteins. After incubation at 27° C. for about 88 h, the fermentation broth was collected and centrifuged at 3,000 rpm for 15 min. The supernatant was discarded, and the cells were washed with PBS for use in expression, identification and purification. Methods of infection and expression were publicly available, for example, the patent CN 101148661 B.

Example 4: Expression and Identification of C-Terminus Modified HPV6L1

1×10$^6$ cells expressing the different C-terminus modified HPV6L1 described in Example 3 respectively were collected and resuspended in 200 μl PBS solution. 50 μl of 6× loading buffer was added and the samples were denatured at 75° C. for 8 minutes. 10 μl of sample was used for SDS-PAGE electrophoresis and Western blot identification, respectively. The results were as shown in FIG. 1. All 8 C-terminus modified HPV6L1 proteins could be expressed in insect cells, with a size of about 55 kDa. Methods of SDS-PAGE electrophoresis and Western blot identification were publicly available, for example, the patent CN 101148661 B.

Example 5: Comparison of Expression Amounts Between C-Terminus Modified HPV6L1 Proteins and Wild-Type HPV6L1 Protein 1×10$^6$ cells expressing the C-terminus modified HPV6L1 proteins and wild-type HPV6L1 described in Example 3 respectively were collected and resuspended in 200 μl PBS solution. The cells were sonicated by ultrasonic disruption (Ningbo Scientz Ultrasonic Cell Disruptor, 2 #probe, 100 W, ultrasound 5 s, interval 7 s, total period 3 min) and centrifuged at a high speed of 12,000 rpm for 10 minutes. The lysed supernatant was collected and the L1 content in the supernatant was detected by sandwich ELISA, which was well known, for example, the patent CN104513826A.

Microtiter plates were coated with HPV6L1 monoclonal antibodies prepared by the inventor at 80 ng/well by overnight incubation at 4° C. The plate was blocked with 5% BSA-PBST at room temperature for 2 h and washed 3 times with PBST. The lysed supernatant was subjected to 2-fold serial dilution with PBS. The HPV6L1 VLP standard was also subjected to serial dilution from a concentration of 2 μg/ml to 0.0625 μg/ml. The diluted samples were added to the plate respectively at 100 μl per well and incubated at 37° C. for 1 h. The plate was washed 3 times with PBST, and 1:3000 diluted HPV6L1 rabbit polyclonal antibody was added at 100 μl per well and incubated at 37° C. for 1 h. The plate was washed 3 times with PBST, and 1:3000 diluted HRP-labeled goat anti-mouse IgG (1:3000 dilution, ZSGB-Bio Corporation) was added and incubated at 37° C. for 45 minutes. The plate was washed 5 times with PBST, and 100 μl of OPD substrate (Sigma) was added to each well for development at 37° C. for 5 minutes. The reaction was stopped with 50 μl of 2 M sulfuric acid, and the absorbance at 490 nm was determined. The concentrations of C-terminus modified HPV6L1 proteins and wild-type HPV6L1 protein in the lysed supernatant were calculated according to the standard curve.

The results were as shown in Table 1. The expression amounts of 6L1CS1, 6L1CS2, 6L1CS3, 6L1CS4, 6L1CS6, 6L1CS7 and 6L1CS8 of the present application were all higher than that of wild-type HPV6L1 protein, and the expression amount of 6L1CS5 was comparable to that of wild-type HPV6L1 protein.

TABLE 1

Analysis of expression amounts of HPV6L1 proteins

| Protein name | Expression amount (mg/L) | | | |
|---|---|---|---|---|
| | Batch 1 | Batch 2 | Batch 3 | Average |
| HPV6L1 | 52 | 58 | 49 | 53 |
| 6L1CS1 | 68 | 55 | 62 | 61.7 |
| 6L1CS2 | 195 | 198 | 202 | 198.3 |
| 6L1CS3 | 106 | 128 | 115 | 116.3 |
| 6L1CS4 | 200 | 215 | 203 | 206 |
| 6L1CS5 | 53 | 51 | 45 | 49.7 |
| 6L1CS6 | 208 | 221 | 226 | 218.3 |
| 6L1CS7 | 139 | 153 | 166 | 152.7 |
| 6L1CS8 | 187 | 195 | 180 | 187.3 |

Example 6: Purification and Dynamic Light Scattering Particle Size Analysis of C-Terminus Modified HPV6L1 Proteins 50 ml of cell fermentation broth of wild-type HPV6L1 or C-terminus modified HPV6L1 was collected and the cells were resuspended with 10 ml of PBS. PMSF was added to a final concentration of 1 mg/ml. The cells were ultrasonically disrupted (Ningbo Scientz Ultrasonic Cell Disruptor, 6 #probe, 100 W, ultrasound 5 s, interval 7 s, total period 5 min) and the disrupted supernatant was collected for purification. The purification steps were carried out at room temperature. 4% (3-mercaptoethanol (w/w) was added to the lysate to depolymerize VLP. Then the samples were filtered with 0.22 μm filters, followed by successive purification with DMAE anion exchange chromatography (20 mM Tris, 180 mM NaCl, 4% (3-ME, elution at pH 7.9), TMAE anion exchange chromatography (20 mM Tris, 180 mM NaCl, 4% (3-ME, elution at pH 7.9) and hydroxyapatite chromatography (100 mM NaH.sub.2PO.sub.4, 30 mM NaCl, 4% (3-ME, elution at pH 6.0). The purified product was concentrated using Planova™ ultrafiltration system, and buffer (20 mM NaH.sub.2PO.sub.4, 500 mM NaCl, pH 6.0) exchange was performed to faciliate VLP assembly. The purification yields of 6L1CS1, 6L1CS2, 6L1CS3, 6L1CS4, 6L1CS6, 6L1CS7 and 6L1CS8 were 25-50 mg/L, the purification yield of 6L1CS5 was 15 mg/L, while the purification yield of wild-type HPV6L1 was only 8 mg/L. The above purification methods were all publicly available.

Figure 2A:
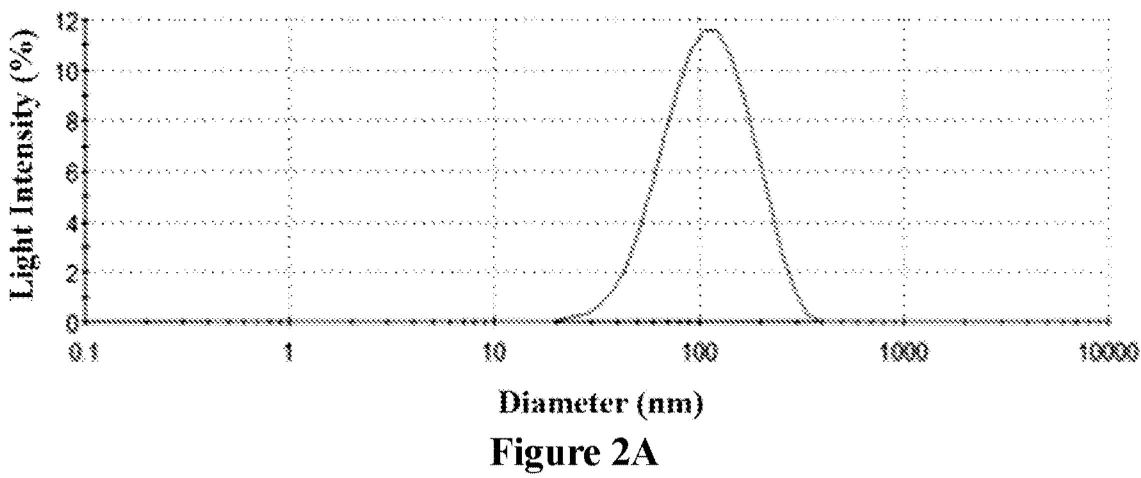
FIGS. 2A to 2C show the dynamic light scattering analysis results of wild-type HPV6L1, 6L1CS4 and 6L1CS6 mutant proteins obtained after purification in Example 6 of the present application. The results show that the hydraulic diameters of the virus-like particles formed by wild-type HPV6L1, 6L1CS4 and 6L1CS6 recombinant proteins are 97.48 nm, 131.3 nm and 127.1 nm, respectively, and the percentages of particle assembly are all 100%.
Figure 2B:
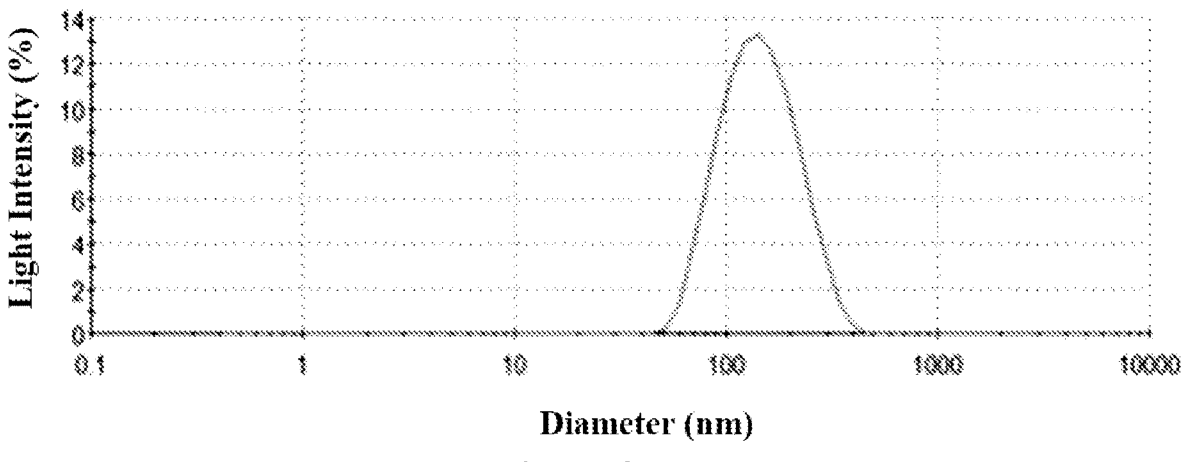
Figure 2C:
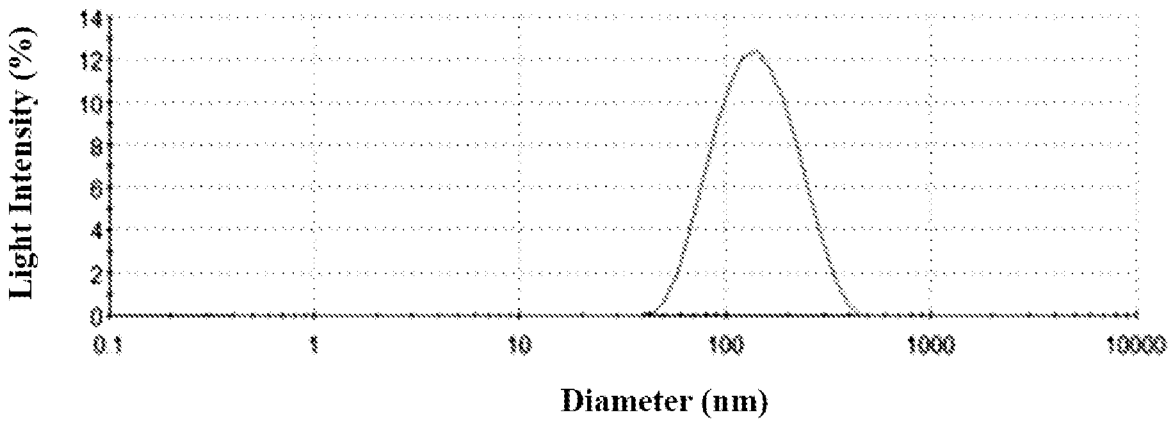

The purified wild-type HPV6L1 protein or C-terminus modified HPV6L1 protein solutions were subjected to DLS particle size analysis (Zetasizer Nano ZS 90™ Dynamic Light Scatterer, Malvern), and the results were as shown in Table 2, wherein the DLS analysis plots of wild-type HPV6L1, 6L1CS4 and 6L1CS6 were as shown in FIGS. 2A to 2C.

TABLE 2

DLS analysis of HPV6L1 proteins

| Protein name | Hydraulic diameter (nm) | PDI |
|---|---|---|
| HPV6L1 | 97.48 | 0.181 |
| 6L1CS1 | 104.3 | 0.152 |
| 6L1CS2 | 112.6 | 0.115 |
| 6L1CS3 | 135.4 | 0.133 |
| 6L1CS4 | 131.3 | 0.188 |
| 6L1CS5 | 109.4 | 0.163 |
| 6L1CS6 | 127.1 | 0.170 |
| 6L1CS7 | 99.2 | 0.108 |
| 6L1CS8 | 115.6 | 0.122 |

Figure 3A:
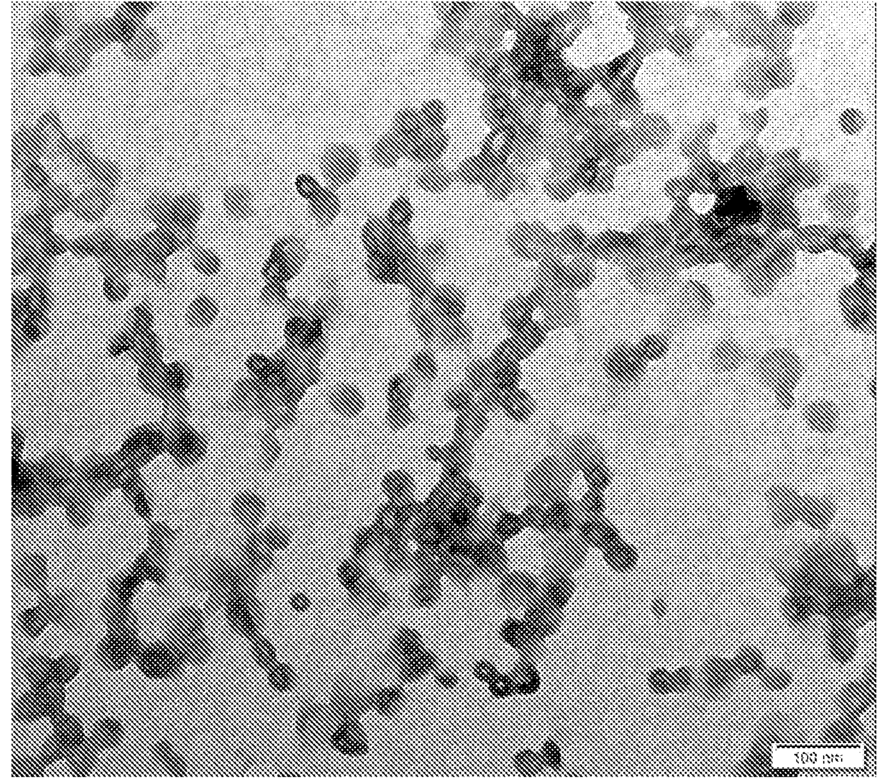
FIGS. 3A to 3B show the transmission electron microscopy observation results of 6L1CS4 and 6L1CS6 VLPs obtained after purification in Example 7 of the present application. A large number of virus-like particles with diameters of about 30-55 nm can be seen in the field. The particle size is consistent with the theoretical value and has good uniformity. Bar=100 nm.
Figure 3B:
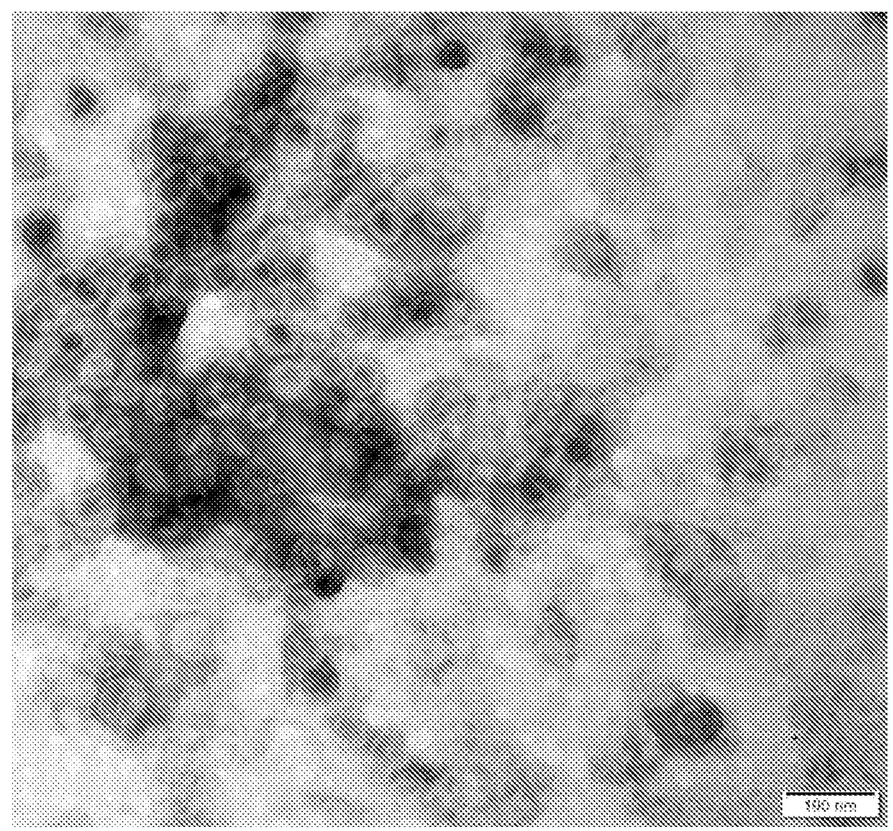

Example 7: Transmission Electron Microscopy Observation of C-Terminus Modified HPV6L1 VLPs The C-terminus modified HPV6L1 VLPs were purified respectively according to the chromatographic purification method described in Example 6. The VLPs after dialysis were prepared on copper mesh, stained with 1% uranium acetate, fully dried and then observed using JEM-1400 electron microscope (Olympus). Some of the results were as shown in FIGS. 3A to 3B. The C-terminus modified HPV6L1 VLPs were approximately 30-55 nm in diameter and had a regular shape. Methods of copper mesh preparation and electron microscopy observation were all publicly available, for example, the patent CN 101148661 B.

Example 8: Immunization of Mice with C-Terminus Modified HPV6L1 VLPs and Determination of Neutralizing Antibody Titers 4-6 weeks old BALB/c mice were randomly divided into groups of 5 mice and immunized with wild-type HPV6L1 VLP and the C-terminus modified HPV6L1 VLPs respectively. L1 VLP was intramuscularly injected at an immunizing dose of 0.1 μg at Week 0 and Week 2 for a total of 2 doses. Tail vein blood was collected 2 weeks after the second immunization and serum was isolated.

Figure 4:
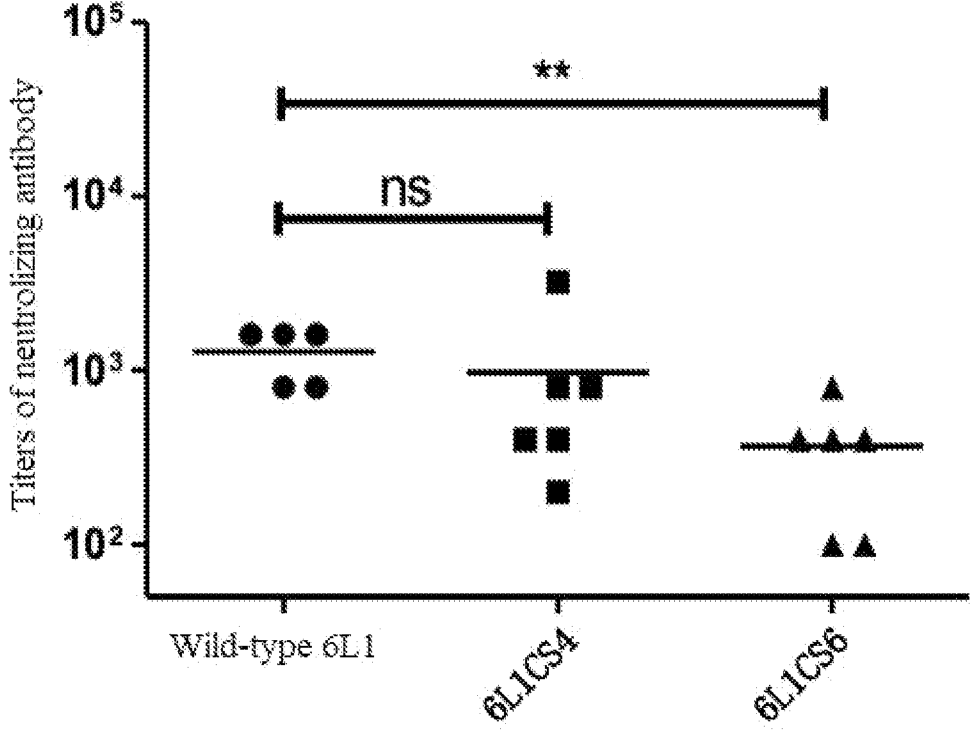
FIG. 4 shows the analysis of neutralizing antibody titers in immune serum of mice inoculated with wild-type HPV6L1, 6L1CS4 and 6L1CS6 VLPs in Example 8 of the present application. ns: $P>0.05$, **: $P<0.01$.

HPV6 pseudovirus was used to detect HPV6 neutralizing antibody titers in immune serum, and the results were as shown in FIG. 4. Wild-type HPV6L1 VLP, 6L1CS4 VLP and 6L1CS6 VLP were all effective in inducing neutralizing antibodies in immunized mice, among which the neutralizing antibody titers induced by 6L1CS4 VLP and wild-type HPV6L1 VLP were not significantly different, and the neutralizing antibody titer induced by 6L1CS6 VLP was significantly lower than that induced by wild-type HPV6L1 VLP ($P<0.01$). After immunizing mice with the other six types of C-terminus modified HPV6L1 mutant VLPs of the present application according to the above-mentioned strategies, the HPV6 neutralizing antibody levels induced were all between 400 and 1600, with no difference from that induced by wild-type HPV6L1 VLP.

In summary, the inventor found that the expression levels of mutants obtained by C-terminus amino acid substitution modification of HPV6L1 vary from each other, and are irregular. There is also a certain difference in the immune activities among the VLPs assembled thereby. Therefore, it cannot be expected that HPV6L1 mutants with high expression level, effective assembly and good immune activity can be obtained by the method of C-terminus substitution modification. The HPV6L1 mutants of the present application obtained by C-terminus amino acid substitution modification can be used in the formulation of multivalent HPV prophylactic vaccine and in the construction of broad-spectrum HPV prophylactic vaccine, and has good research and development prospects.

Description of Sequences

SEQ ID No. 1: HPV6L1
MWRPSDSTVY VPPPNPVSKV VATDAYVTRT NIFYHASSSR LLAVGHPYFS
IKRANKTVVP KVSGYQYRVF KVVLPDPNKF ALPDSSLFDP TTQRLVWACT
GLEVGRGQPL GVGVSGHPFL NKYDDVENSG SGGNPGQDNR VNVGMDYKQT
QLCMVGCAPP LGEHWGKGKQ CTNTPVQAGD CPPLELITSV IQDGDMVDTG
FGAMNFADLQ TNKSDVPIDI CGTTCKYPDY LQMAADPYGD RLFFFLRKEQ
MFARHFFNRA GEVGEPVPDT LIIKGSGNRT SVGSSIYVNT PSGSLVSSEA
QLFNKPYWLQ KAQGHNNGIC WGNQLFVTVV DTTRSTNMTL CASVTTSSTY
TNSDYKEYMR HVEEYDLQFI FQLCSITLSA EVMAYIHTMN PSVLEDWNFG
LSPPPNGTLE DTYRYVQSQA ITCQKPTPEK EKPDPYKNLS FWEVNLKEKF
SSELDQYPLG RKFLLQSGYR GRSSIRTGVK RPAVSKASAA PKRKRAKTKR

SEQ ID No. 2: 6LICS1
1 MWRPSDSTVY VPPPNPVSKV
21 VATDAYVTRT NIFYHASSSR
41 LLAVGHPYFS IKRANKTVVP
61 KVSGYQYRVF KVVLPDPNKF
81 ALPDSSLFDP TTQRLVWACT
101 GLEVGRGQPL GVGVSGHPFL
121 NKYDDVENSG SGGNPGQDNR
141 VNVGMDYKQT QLCMVGCAPP
161 LGEHWGKGKQ CTNTPVQAGD
181 CPPLELITSV IQDGDMVDTG
201 FGAMNFADLQ TNKSDVPIDI
221 CGTTCKYPDY LQMAADPYGD
241 RLFFFLRKEQ MFARHFFNRA
261 GEVGEPVPDT LIIKGSGNRT
281 SVGSSIYVNT PSGSLVSSEA
301 QLFNKPYWLQ KAQGHNNGIC
321 WGNQLFVTVV DTTRSTNMTL
341 CASVTTSSTY TNSDYKEYMR
361 HVEEYDLQFI FQLCSITLSA
381 EVMAYIHTMN PSVLEDWNFG
401 LSPPPNGTLE DTYRYVQSQA
421 ITCQKPTPEK EKPDPYKNLS
441 FWEVNLKEKF SSELDQYPLG
461 RKFLLQSGYG GRSSIATGVG
481 APAVSGASAA PAGAAAGTKR

SEQ ID No. 3: 6LICS2
1 MWRPSDSTVY VPPPNPVSKV
21 VATDAYVTRT NIFYHASSSR
41 LLAVGHPYFS IKRANKTVVP
61 KVSGYQYRVF KVVLPDPNKF
81 ALPDSSLFDP TTQRLVWACT
101 GLEVGRGQPL GVGVSGHPFL
121 NKYDDVENSG SGGNPGQDNR
141 VNVGMDYKQT QLCMVGCAPP
161 LGEHWGKGKQ CTNTPVQAGD
181 CPPLELITSV IQDGDMVDTG
201 FGAMNFADLQ TNKSDVPIDI
221 CGTTCKYPDY LQMAADPYGD
241 RLFFFLRKEQ MFARHFFNRA
261 GEVGEPVPDT LIIKGSGNRT
281 SVGSSIYVNT PSGSLVSSEA
301 QLFNKPYWLQ KAQGHNNGIC
321 WGNQLFVTVV DTTRSTNMTL
341 CASVTTSSTY TNSDYKEYMR
361 HVEEYDLQFI FQLCSITLSA
381 EVMAYIHTMN PSVLEDWNFG
401 LSPPPNGTLE DTYRYVQSQA
421 ITCQKPTPEK EKPDPYKNLS
441 FWEVNLKEKF SSELDQYPLG
461 RKFLLQSGYR GGSSIRTGVG
481 SPAVSKASAA PDGSGAGTKR

SEQ ID No. 4: 6LICS3
1 MWRPSDSTVY VPPPNPVSKV
21 VATDAYVTRT NIFYHASSSR
41 LLAVGHPYFS IKRANKTVVP
61 KVSGYQYRVF KVVLPDPNKF
81 ALPDSSLFDP TTQRLVWACT
101 GLEVGRGQPL GVGVSGHPFL
121 NKYDDVENSG SGGNPGQDNR
141 VNVGMDYKQT QLCMVGCAPP
161 LGEHWGKGKQ CTNTPVQAGD
181 CPPLELITSV IQDGDMVDTG
201 FGAMNFADLQ TNKSDVPIDI

-continued

```
221     CGTTCKYPDY LQMAADPYGD
241     RLFFFLRKEQ MFARHFFNRA
261     GEVGEPVPDT LIIKGSGNRT
281     SVGSSIYVNT PSGSLVSSEA
301     QLFNKPYWLQ KAQGHNNGIC
321     WGNQLFVTVV DTTRSTNMTL
341     CASVTTSSTY TNSDYKEYMR
361     HVEEYDLQFI FQLCSITLSA
381     EVMAYIHTMN PSVLEDWNFG
401     LSPPPNGTLE DTYRYVQSQA
421     ITCQKPTPEK EKPDPYKNLS
441     FWEVNLKEKF SSELDQYPLG
461     RKFLLQSGYR GGSSIRTGVD
481     GPAVSKASAA PDGSRAGTKR
```

SEQ ID No. 5: 6LICS4

```
  1     MWRPSDSTVY VPPPNPVSKV
 21     VATDAYVTRT NIFYHASSSR
 41     LLAVGHPYFS IKRANKTVVP
 61     KVSGYQYRVF KVVLPDPNKF
 81     ALPDSSLFDP TTQRLVWACT
101     GLEVGRGQPL GVGVSGHPFL
121     NKYDDVENSG SGGNPGQDNR
141     VNVGMDYKQT QLCMVGCAPP
161     LGEHWGKGKQ CTNTPVQAGD
181     CPPLELITSV IQDGDMVDTG
201     FGAMNFADLQ TNKSDVPIDI
221     CGTTCKYPDY LQMAADPYGD
241     RLFFFLRKEQ MFARHFFNRA
261     GEVGEPVPDT LIIKGSGNRT
281     SVGSSIYVNT PSGSLVSSEA
301     QLFNKPYWLQ KAQGHNNGIC
321     WGNQLFVTVV DTTRSTNMTL
341     CASVTTSSTY TNSDYKEYMR
361     HVEEYDLQFI FQLCSITLSA
381     EVMAYIHTMN PSVLEDWNFG
401     LSPPPNGTLE DTYRYVQSQA
421     ITCQKPTPEK EKPDPYKNLS
441     FWEVNLKEKF SSELDQYPLG
461     RKFLLQSGYR GGSSIRTGVG
481     SPAVSKASAA PDGSRADTKR
```

SEQ ID No. 6: 6LICS5

```
  1     MWRPSDSTVY VPPPNPVSKV
 21     VATDAYVTRT NIFYHASSSR
 41     LLAVGHPYFS IKRANKTVVP
 61     KVSGYQYRVF KVVLPDPNKF
 81     ALPDSSLFDP TTQRLVWACT
101     GLEVGRGQPL GVGVSGHPFL
121     NKYDDVENSG SGGNPGQDNR
141     VNVGMDYKQT QLCMVGCAPP
161     LGEHWGKGKQ CTNTPVQAGD
181     CPPLELITSV IQDGDMVDTG
201     FGAMNFADLQ TNKSDVPIDI
221     CGTTCKYPDY LQMAADPYGD
241     RLFFFLRKEQ MFARHFFNRA
261     GEVGEPVPDT LIIKGSGNRT
281     SVGSSIYVNT PSGSLVSSEA
301     QLFNKPYWLQ KAQGHNNGIC
321     WGNQLFVTVV DTTRSTNMTL
341     CASVTTSSTY TNSDYKEYMR
361     HVEEYDLQFI FQLCSITLSA
381     EVMAYIHTMN PSVLEDWNFG
401     LSPPPNGTLE DTYRYVQSQA
421     ITCQKPTPEK EKPDPYKNLS
441     FWEVNLKEKF SSELDQYPLG
461     RKFLLQSGYR GGSSIRTGVD
481     GPAVSKASAA PDGSRADTKR
```

SEQ ID No. 7: 6LICS6

```
  1     MWRPSDSTVY VPPPNPVSKV
 21     VATDAYVTRT NIFYHASSSR
 41     LLAVGHPYFS IKRANKTVVP
 61     KVSGYQYRVF KVVLPDPNKF
 81     ALPDSSLFDP TTQRLVWACT
101     GLEVGRGQPL GVGVSGHPFL
121     NKYDDVENSG SGGNPGQDNR
141     VNVGMDYKQT QLCMVGCAPP
161     LGEHWGKGKQ CTNTPVQAGD
```

-continued

```
181     CPPLELITSV IQDGDMVDTG
201     FGAMNFADLQ TNKSDVPIDI
221     CGTTCKYPDY LQMAADPYGD
241     RLFFFLRKEQ MFARHFFNRA
261     GEVGEPVPDT LIIKGSGNRT
281     SVGSSIYVNT PSGSLVSSEA
301     QLFNKPYWLQ KAQGHNNGIC
321     WGNQLFVTVV DTTRSTNMTL
341     CASVTTSSTY TNSDYKEYMR
361     HVEEYDLQFI FQLCSITLSA
381     EVMAYIHTMN PSVLEDWNFG
401     LSPPPNGTLE DTYRYVQSQA
421     ITCQKPTPEK EKPDPYKNLS
441     FWEVNLKEKF SSELDQYPLG
461     RKFLLQSGYR GGSSIRTGVG
481     SPAVSSASAA PSGSGAGTGR
```

SEQ ID No. 8: 6LICS7

```
  1     MWRPSDSTVY VPPPNPVSKV
 21     VATDAYVTRT NIFYHASSSR
 41     LLAVGHPYFS IKRANKTVVP
 61     KVSGYQYRVF KVVLPDPNKF
 81     ALPDSSLFDP TTQRLVWACT
101     GLEVGRGQPL GVGVSGHPFL
121     NKYDDVENSG SGGNPGQDNR
141     VNVGMDYKQT QLCMVGCAPP
161     LGEHWGKGKQ CTNTPVQAGD
181     CPPLELITSV IQDGDMVDTG
201     FGAMNFADLQ TNKSDVPIDI
221     CGTTCKYPDY LQMAADPYGD
241     RLFFFLRKEQ MFARHFFNRA
261     GEVGEPVPDT LIIKGSGNRT
281     SVGSSIYVNT PSGSLVSSEA
301     QLFNKPYWLQ KAQGHNNGIC
321     WGNQLFVTVV DTTRSTNMTL
341     CASVTTSSTY TNSDYKEYMR
361     HVEEYDLQFI FQLCSITLSA
381     EVMAYIHTMN PSVLEDWNFG
401     LSPPPNGTLE DTYRYVQSQA
421     ITCQKPTPEK EKPDPYKNLS
441     FWEVNLKEKF SSELDQYPLG
461     RKFLLQSGYR GGSSIATGVD
481     GPAVSKASAA PSGSGAGTKR
```

SEQ ID No. 9: 6LICS8

```
  1     MWRPSDSTVY VPPPNPVSKV
 21     VATDAYVTRT NIFYHASSSR
 41     LLAVGHPYFS IKRANKTVVP
 61     KVSGYQYRVF KVVLPDPNKF
 81     ALPDSSLFDP TTQRLVWACT
101     GLEVGRGQPL GVGVSGHPFL
121     NKYDDVENSG SGGNPGQDNR
141     VNVGMDYKQT QLCMVGCAPP
161     LGEHWGKGKQ CTNTPVQAGD
181     CPPLELITSV IQDGDMVDTG
201     FGAMNFADLQ TNKSDVPIDI
221     CGTTCKYPDY LQMAADPYGD
241     RLFFFLRKEQ MFARHFFNRA
261     GEVGEPVPDT LIIKGSGNRT
281     SVGSSIYVNT PSGSLVSSEA
301     QLFNKPYWLQ KAQGHNNGIC
321     WGNQLFVTVV DTTRSTNMTL
341     CASVTTSSTY TNSDYKEYMR
361     HVEEYDLQFI FQLCSITLSA
381     EVMAYIHTMN PSVLEDWNFG
401     LSPPPNGTLE DTYRYVQSQA
421     ITCQKPTPEK EKPDPYKNLS
441     FWEVNLKEKF SSELDQYPLG
461     RKFLLQSGYR GDSSIRTGVD
481     RPAVSKASAA PDAKSAKTGR
```

SEQ ID No. 10: 6L1CS1nt

```
ATG TGG CGT CCC TCA GAT TCA ACC GTG TAC GTC CCC CCC CCT AAT CCC
GTG TCC AAA GTC GTC GCT ACC GAC GCC TAC GTC ACC AGG ACA AAT
ATC TTC TAC CAC GCT TCA TCC AGC CGC TTG TTG GCC GTC GGC CAC
CCC TAC TTC AGC ATT AAG CGC GCT AAT AAG ACC GTC GTG CCC AAA
GTC AGC GGC TAC CAG TAC CGC GTC TTC AAA GTG GTC CTC CCC GAC
CCC AAT AAA TTC GCC CTG CCC GAC AGC TCC CTC TTC GAT CCT ACC ACC
CAA AGG CTG GTG TGG GCC TGT ACC GGC CTC GAA GTG GGT CGC GGC
```

-continued

CAG CCC CTG GGT GTC GGC GTC TCC GGC CAC CCC TTC TTG AAT AAG
TAC GAC GAC GTG GAG AAC TCC GGC TCC GGC GGC AAC CCC GGC CAA
GAC AAC CGC GTC AAC GTG GGC ATG GAC TAC AAG CAG ACA CAA TTG
TGC ATG GTC GGT TGC GCC CCC CCC CTG GGC GAG CAC TGG GGC AAA
GGC AAG CAG TGC ACC AAC ACA CCT GTG CAG GCT GGC GAT TGT CCT
CCC CTC GAG TTG ATC ACA TCC GTC ATC CAA GAC GGC GAT ATG GTC
GAC ACC GGT TTC GGC GCC ATG AAC TTC GCC GAT CTG CAG ACA AAC
AAG AGC GAC GTC CCT ATC GAC ATC TGC GGC ACC ACC TGT AAG TAC
CCC GAC TAC CTC CAG ATG GCC GCC GAT CCC TAC GGC GAC CGC CTC
TTC TTC TTC CTC AGG AAA GAG CAG ATG TTC GCC CGC CAT TTC TTC AAC
CGC GCT GGC GAG GTC GGC GAG CCC GTC CCC GAC ACC CTC ATC ATC
AAG GGC TCC GGT AAT CGC ACC AGC GTG GGC TCC TCC ATC TAC GTG
AAC ACC CCC TCC GGT AGC CTC GTC AGC AGC GAA GCC CAG CTG TTC
AAC AAG CCC TAC TGG TTG CAG AAA GCC CAA GGC CAC AAT AAC GGC
ATC TGT TGG GGC AAT CAG CTC TTC GTC ACC GTC GTG GAC ACA ACC
AGG TCC ACC AAC ATG ACC TTG TGC GCC AGC GTC ACC ACC AGC TCC
ACC TAC ACC AAC AGC GAC TAC AAA GAG TAC ATG AGG CAC GTC GAA
GAA TAC GAC CTG CAA TTC ATC TTC CAG CTC TGC TCA ATC ACC CTG AGC
GCC GAG GTG ATG GCT TAC ATC CAT ACC ATG AAC CCC AGC GTC CTC
GAA GAT TGG AAT TTC GGT CTG AGC CCC CCC CCC AAC GGC ACC CTC
GAA GAC ACC TAC CGC TAC GTG CAA AGC CAA GCT ATC ACA TGC CAA
AAG CCT ACC CCC GAG AAG GAG AAG CCA GAC CCT TAC AAA AAC CTG
TCC TTC TGG GAA GTC AAT CTG AAG GAG AAA TTC AGC TCC GAG CTG
GAC CAA TAC CCT TTG GGC AGG AAA TTC CTG CTC CAG TCC GGC TAC
GGA GGC CGA TCC AGC ATC GCA ACC GGC GTG GGA GCA CCC GCC GTC
AGC GGA GCT AGC GCC GCT CCT GCA GGA GCC GCA GCT GGG ACA
AAG CGT TAAT

SEQ ID No. 11: 6L1CS2nt
ATG TGG CGT CCC TCA GAT TCA ACC GTG TAC GTC CCC CCC CCT AAT CCC
GTG TCC AAA GTC GTC GCT ACC GAC GCC TAC GTC ACC AGG ACA AAT
ATC TTC TAC CAC GCT TCA TCC AGC CGC TTG TTG GCC GTC GGC CAC
CCC TAC TTC AGC ATT AAG CGC GCT AAT AAG ACC GTC GTG CCC AAA
GTC AGC GGC
TAC CAG TAC CGC GTC TTC AAA GTG GTC CTC CCC GAC CCC AAT AAA
TTC GCC CTG CCC GAC AGC TCC CTC TTC GAT CCT ACC ACC CAA AGG
CTG GTG TGG GCC TGT ACC GGC CTC GAA GTG GGT CGC GGC CAG CCC
CTG GGT GTC GGC GTC TCC GGC CAC CCC TTC TTG AAT AAG TAC GAC
GAC GTG GAG AAC TCC GGC TCC GGC GGC AAC CCC GGC CAA GAC AAC
CGC GTC AAC GTG GGC ATG GAC TAC AAG CAG ACA CAA TTG TGC ATG
GTC GGT TGC GCC CCC CCC CTG GGC GAG CAC TGG GGC AAA GGC AAG
CAG TGC ACC AAC ACA CCT GTG CAG GCT GGC GAT TGT CCT CCC CTC
GAG TTG ATC ACA TCC GTC ATC CAA GAC GGC GAT ATG GTC GAC ACC
GGT TTC GGC GCC ATG AAC TTC GCC GAT CTG CAG ACA AAC AAG AGC
GAC GTC CCT ATC GAC ATC TGC GGC ACC ACC TGT AAG TAC CCC GAC
TAC CTC CAG ATG GCC GCC GAT CCC TAC GGC GAC CGC CTC TTC TTC TTC
CTC AGG AAA GAG CAG ATG TTC GCC CGC CAT TTC TTC AAC CGC GCT
GGC GAG GTC GGC GAG CCC GTC CCC GAC ACC CTC ATC ATC AAG GGC
TCC GGT AAT CGC ACC AGC GTG GGC TCC TCC ATC TAC GTG AAC ACC
CCC TCC GGT AGC CTC GTC AGC AGC GAA GCC CAG CTG TTC AAC AAG
CCC TAC TGG TTG CAG AAA GCC CAA GGC CAC AAT AAC GGC ATC TGT
TGG GGC AAT CAG CTC TTC GTC ACC GTC GTG GAC ACA ACC AGG TCC
ACC AAC ATG ACC TTG TGC GCC AGC GTC ACC ACC AGC TCC ACC TAC
ACC AAC AGC GAC TAC AAA GAG TAC ATG AGG CAC GTC GAA GAA TAC
GAC CTG CAA TTC ATC TTC CAG CTC TGC TCA ATC ACC CTG AGC GCC
GAG GTG ATG GCT TAC ATC CAT ACC ATG AAC CCC AGC GTC CTC GAA
GAT TGG AAT TTC GGT CTG AGC CCC CCC CCC AAC GGC ACC CTC GAA
GAC ACC TAC CGC TAC GTG CAA AGC CAA GCT ATC ACA TGC CAA AAG
CCT ACC CCC GAG AAG GAG AAG CCA GAC CCT TAC AAA AAC CTG TCC
TTC TGG GAA GTC AAT CTG AAG GAG AAA TTC AGC TCC GAG CTG GAC
CAA TAC CCT TTG GGC AGG AAA TTC CTG CTC CAG TCC GGC TAC CGA
GGC GGA TCC AGC ATC CGA ACC GGC GTG GGA AGT CCC GCC GTC AGC
AAG GCT AGC GCC GCT CCT GAT GGA AGC GGA GCT GGG ACA AAG CGT
TAAT

SEQ ID No. 12: 6L1CS3nt
ATG TGG CGT CCC TCA GAT TCA ACC GTG TAC GTC CCC CCC CCT AAT CCC
GTG TCC AAA GTC GTC GCT ACC GAC GCC TAC GTC ACC AGG ACA AAT
ATC TTC TAC CAC GCT TCA TCC AGC CGC TTG TTG GCC GTC GGC CAC
CCC TAC TTC AGC ATT AAG CGC GCT AAT AAG ACC GTC GTG CCC AAA
GTC AGC GGC TAC CAG TAC CGC GTC TTC AAA GTG GTC CTC CCC GAC
CCC AAT AAA TTC GCC CTG CCC GAC AGC TCC CTC TTC GAT CCT ACC ACC
CAA AGG CTG GTG TGG GCC TGT ACC GGC CTC GAA GTG GGT CGC GGC
CAG CCC CTG GGT GTC GGC GTC TCC GGC CAC CCC TTC TTG AAT AAG
TAC GAC GAC GTG GAG AAC TCC GGC TCC GGC GGC AAC CCC GGC CAA
GAC AAC CGC GTC AAC GTG GGC ATG GAC TAC AAG CAG ACA CAA TTG
TGC ATG GTC GGT TGC GCC CCC CCC CTG GGC GAG CAC TGG GGC AAA
GGC AAG CAG TGC ACC AAC ACA CCT GTG CAG GCT GGC GAT TGT CCT
CCC CTC GAG TTG ATC ACA TCC GTC ATC CAA GAC GGC GAT ATG GTC

GAC ACC GGT TTC GGC GCC ATG AAC TTC GCC GAT CTG CAG ACA AAC
AAG AGC GAC GTC CCT ATC GAC ATC TGC GGC ACC ACC TGT AAG TAC
CCC GAC TAC CTC CAG ATG GCC GCC GAT CCC TAC GGC GAC CGC CTC
TTC TTC TTC CTC AGG AAA GAG CAG ATG TTC GCC CGC CAT TTC TTC AAC
CGC GCT GGC GAG GTC GGC GAG CCC GTC CCC GAC ACC CTC ATC ATC
AAG GGC TCC GGT AAT CGC ACC AGC GTG GGC TCC TCC ATC TAC GTG
AAC ACC CCC TCC GGT AGC CTC GTC AGC AGC GAA GCC CAG CTG TTC
AAC AAG CCC TAC TGG TTG CAG AAA GCC CAA GGC CAC AAT AAC GGC
ATC TGT TGG GGC AAT CAG CTC TTC GTC ACC GTC GTG GAC ACA ACC
AGG TCC ACC AAC ATG ACC TTG TGC GCC AGC GTC ACC ACC AGC TCC
ACC TAC ACC AAC AGC GAC TAC AAA GAG TAC ATG AGG CAC GTC GAA
GAA TAC GAC CTG CAA TTC ATC TTC CAG CTC TGC TCA ATC ACC CTG AGC
GCC GAG GTG ATG GCT TAC ATC CAT ACC ATG AAC CCC AGC GTC CTC
GAA GAT TGG AAT TTC GGT CTG AGC CCC CCC CCC AAC GGC ACC CTC
GAA GAC ACC TAC CGC TAC GTG CAA AGC CAA GCT ATC ACA TGC CAA
AAG CCT ACC CCC GAG AAG GAG AAG CCA GAC CCT TAC AAA AAC CTG
TCC TTC TGG GAA GTC AAT CTG AAG GAG AAA TTC AGC TCC GAG CTG
GAC CAA TAC CCT TTG GGC AGG AAA TTC CTG CTC CAG TCC GGC TAC
CGA GGC GGA TCC AGC ATC CGA ACC GGC GTG GAT GGA CCC GCC GTC
AGC AAG GCT AGC GCC GCT CCT GAT GGA AGC AGA GCT GGG ACA AAG
CGT TAAT

SEQ ID No. 13: 6L1CS4nt
ATG TGG CGT CCC TCA GAT TCA ACC GTG TAC GTC CCC CCC CCT AAT CCC
GTG TCC AAA GTC GTC GCT ACC GAC GCC TAC GTC ACC AGG ACA AAT
ATC TTC TAC CAC GCT TCA TCC AGC CGC TTG TTG GCC GTC GGC CAC
CCC TAC TTC AGC ATT AAG CGC GCT AAT AAG ACC GTC GTG CCC AAA
GTC AGC GGC TAC CAG TAC CGC GTC TTC AAA GTG GTC CTC CCC GAC
CCC AAT AAA TTC GCC CTG CCC GAC AGC TCC CTC TTC GAT CCT ACC ACC
CAA AGG CTG GTG TGG GCC TGT ACC GGC CTC GAA GTG GGT CGC GGC
CAG CCC CTG GGT GTC GGC GTC TCC GGC CAC CCC TTC TTG AAT AAG
TAC GAC GAC GTG GAG AAC TCC GGC TCC GGC GGC AAC CCC GGC CAA
GAC AAC CGC GTC AAC GTG GGC ATG GAC TAC AAG CAG ACA CAA TTG
TGC ATG GTC GGT TGC GCC CCC CCC CTG GGC GAG CAC TGG GGC AAA
GGC AAG CAG TGC ACC AAC ACA CCT GTG CAG GCT GGC GAT TGT CCT
CCC CTC GAG TTG ATC ACA TCC GTC ATC CAA GAC GGC GAT ATG GTC
GAC ACC GGT TTC GGC GCC ATG AAC TTC GCC GAT CTG CAG ACA AAC
AAG AGC GAC GTC CCT ATC GAC ATC TGC GGC ACC ACC TGT AAG TAC
CCC GAC TAC CTC CAG ATG GCC GCC GAT CCC TAC GGC GAC CGC CTC
TTC TTC TTC CTC AGG AAA GAG CAG ATG TTC GCC CGC CAT TTC TTC AAC
CGC GCT GGC GAG GTC GGC GAG CCC GTC CCC GAC ACC CTC ATC ATC
AAG GGC TCC GGT AAT CGC ACC AGC GTG GGC TCC TCC ATC TAC GTG
AAC ACC CCC TCC GGT AGC CTC GTC AGC AGC GAA GCC CAG CTG TTC
AAC AAG CCC TAC TGG TTG CAG AAA GCC CAA GGC CAC AAT AAC GGC
ATC TGT TGG GGC AAT CAG CTC TTC GTC ACC GTC GTG GAC ACA ACC
AGG TCC ACC AAC ATG ACC TTG TGC GCC AGC GTC ACC ACC AGC TCC
ACC TAC ACC AAC AGC GAC TAC AAA GAG TAC ATG AGG CAC GTC GAA
GAA TAC GAC CTG CAA TTC ATC TTC CAG CTC TGC TCA ATC ACC CTG AGC
GCC GAG GTG ATG GCT TAC ATC CAT ACC ATG AAC CCC AGC GTC CTC
GAA GAT TGG AAT TTC GGT CTG AGC CCC CCC CCC AAC GGC ACC CTC
GAA GAC ACC TAC CGC TAC GTG CAA AGC CAA GCT ATC ACA TGC CAA
AAG CCT ACC CCC GAG AAG GAG AAG CCA GAC CCT TAC AAA AAC CTG
TCC TTC TGG GAA GTC AAT CTG AAG GAG AAA TTC AGC TCC GAG CTG
GAC CAA TAC CCT TTG GGC AGG AAA TTC CTG CTC CAG TCC GGC TAC
CGA GGC GGA TCC AGC ATC CGA ACC GGC GTG GGA AGT CCC GCC GTC
AGC AAG GCT AGC GCC GCT CCT GAT GGA AGC AGA GCT GAT ACA AAG
CGT TAAT

SEQ ID No. 14: 6L1CS5nt
ATG TGG CGT CCC TCA GAT TCA ACC GTG TAC GTC CCC CCC CCT AAT CCC
GTG TCC AAA GTC GTC GCT ACC GAC GCC TAC GTC ACC AGG ACA AAT
ATC TTC TAC CAC GCT TCA TCC AGC CGC TTG TTG GCC GTC GGC CAC
CCC TAC TTC AGC ATT AAG CGC GCT AAT AAG ACC GTC GTG CCC AAA
GTC AGC GGC TAC CAG TAC CGC GTC TTC AAA GTG GTC CTC CCC GAC
CCC AAT AAA TTC GCC CTG CCC GAC AGC TCC CTC TTC GAT CCT ACC ACC
CAA AGG CTG GTG TGG GCC TGT ACC GGC CTC GAA GTG GGT CGC GGC
CAG CCC CTG GGT GTC GGC GTC TCC GGC CAC CCC TTC TTG AAT AAG
TAC GAC GAC GTG GAG AAC TCC GGC TCC GGC GGC AAC CCC GGC CAA
GAC AAC CGC GTC AAC GTG GGC ATG GAC TAC AAG CAG ACA CAA TTG
TGC ATG GTC GGT TGC GCC CCC CCC CTG GGC GAG CAC TGG GGC AAA
GGC AAG CAG TGC ACC AAC ACA CCT GTG CAG GCT GGC GAT TGT CCT
CCC CTC GAG TTG ATC ACA TCC GTC ATC CAA GAC GGC GAT ATG GTC
GAC ACC GGT TTC GGC GCC ATG AAC TTC GCC GAT CTG CAG ACA AAC
AAG AGC GAC GTC CCT ATC GAC ATC TGC GGC ACC ACC TGT AAG TAC
CCC GAC TAC CTC CAG ATG GCC GCC GAT CCC TAC GGC GAC CGC CTC
TTC TTC TTC CTC AGG AAA GAG CAG ATG TTC GCC CGC CAT TTC TTC AAC
CGC GCT GGC GAG GTC GGC GAG CCC GTC CCC GAC ACC CTC ATC ATC
AAG GGC TCC GGT AAT CGC ACC AGC GTG GGC TCC TCC ATC TAC GTG
AAC ACC CCC TCC GGT AGC CTC GTC AGC AGC GAA GCC CAG CTG TTC

-continued

AAC AAG CCC TAC TGG TTG CAG AAA GCC CAA GGC CAC AAT AAC GGC
ATC TGT TGG GGC AAT CAG CTC TTC GTC ACC GTC GTG GAC ACA ACC
AGG TCC ACC AAC ATG ACC TTG TGC GCC AGC GTC ACC ACC AGC TCC
ACC TAC ACC AAC AGC GAC TAC AAA GAG TAC ATG AGG CAC GTC GAA
GAA TAC GAC CTG CAA TTC ATC TTC CAG CTC TGC TCA ATC ACC CTG AGC
GCC GAG GTG ATG GCT TAC ATC CAT ACC ATG AAC CCC AGC GTC CTC
GAA GAT TGG AAT TTC GGT CTG AGC CCC CCC CCC AAC GGC ACC CTC
GAA GAC ACC TAC CGC TAC GTG CAA AGC CAA GCT ATC ACA TGC CAA
AAG CCT ACC CCC GAG AAG GAG AAG CCA GAC CCT TAC AAA AAC CTG
TCC TTC TGG GAA GTC AAT CTG AAG GAG AAA TTC AGC TCC GAG CTG
GAC CAA TAC CCT TTG GGC AGG AAA TTC CTG CTC CAG TCC GGC TAC
CGA GGC GGA TCC AGC ATC CGA ACC GGC GTG GAT GGA CCC GCC GTC
AGC AAG GCT AGC GCC GCT CCT GAT GGA AGC AGA GCT GAT ACA AAG
CGT TAAT

SEQ ID No. 15: 6L1CS6nt
ATG TGG CGT CCC TCA GAT TCA ACC GTG TAC GTC CCC CCC CCT AAT CCC
GTG TCC AAA GTC GTC GCT ACC GAC GCC TAC GTC ACC AGG ACA AAT
ATC TTC TAC CAC GCT TCA TCC AGC CGC TTG TTG GCC GTC GGC CAC
CCC TAC TTC AGC ATT AAG CGC GCT AAT AAG ACC GTC GTG CCC AAA
GTC AGC GGC TAC CAG TAC CGC GTC TTC AAA GTG GTC CTC CCC GAC
CCC AAT AAA TTC GCC CTG CCC GAC AGC TCC CTC TTC GAT CCT ACC ACC
CAA AGG CTG GTG TGG GCC TGT ACC GGC CTC GAA GTG GGT CGC GGC
CAG CCC CTG GGT GTC GGC GTC TCC GGC CAC CCC TTC TTG AAT AAG
TAC GAC GAC GTG GAG AAC TCC GGC TCC GGC GGC AAC CCC GGC CAA
GAC AAC CGC GTC AAC GTG GGC ATG GAC TAC AAG CAG ACA CAA TTG
TGC ATG GTC GGT TGC GCC CCC CCC CTG GGC GAG CAC TGG GGC AAA
GGC AAG CAG TGC ACC AAC ACA CCT GTG CAG GCT GGC GAT TGT CCT
CCC CTC GAG TTG ATC ACA TCC GTC ATC CAA GAC GGC GAT ATG GTC
GAC ACC GGT TTC GGC GCC ATG AAC TTC GCC GAT CTG CAG ACA AAC
AAG AGC GAC GTC CCT ATC GAC ATC TGC GGC ACC ACC TGT AAG TAC
CCC GAC TAC CTC CAG ATG GCC GCC GAT CCC TAC GGC GAC CGC CTC
TTC TTC TTC CTC AGG AAA GAG CAG ATG TTC GCC CGC CAT TTC TTC AAC
CGC GCT GGC GAG GTC GGC GAG CCC GTC CCC GAC ACC CTC ATC ATC
AAG GGC TCC GGT AAT CGC ACC AGC GTG GGC TCC TCC ATC TAC GTG
AAC ACC CCC TCC GGT AGC CTC GTC AGC AGC GAA GCC CAG CTG TTC
AAC AAG CCC TAC TGG TTG CAG AAA GCC CAA GGC CAC AAT AAC GGC
ATC TGT TGG GGC AAT CAG CTC TTC GTC ACC GTC GTG GAC ACA ACC
AGG TCC ACC AAC ATG ACC TTG TGC GCC AGC GTC ACC ACC AGC TCC
ACC TAC ACC AAC AGC GAC TAC AAA GAG TAC ATG AGG CAC GTC GAA
GAA TAC GAC CTG CAA TTC ATC TTC CAG CTC TGC TCA ATC ACC CTG AGC
GCC GAG GTG ATG GCT TAC ATC CAT ACC ATG AAC CCC AGC GTC CTC
GAA GAT TGG AAT TTC GGT CTG AGC CCC CCC CCC AAC GGC ACC CTC
GAA GAC ACC TAC CGC TAC GTG CAA AGC CAA GCT ATC ACA TGC CAA
AAG CCT ACC CCC GAG AAG GAG AAG CCA GAC CCT TAC AAA AAC CTG
TCC TTC TGG GAA GTC AAT CTG AAG GAG AAA TTC AGC TCC GAG CTG
GAC CAA TAC CCT TTG GGC AGG AAA TTC CTG CTC CAG TCC GGC TAC
CGA GGC GGA TCC AGC ATC CGA ACC GGC GTGGGA AGT CCC GCC GTC
AGC AGT GCT AGC GCC GCT CCT AGT GGA AGT GGT GCT GGG ACA GGA
CGT TAAT

SEQ ID No. 16: 6L1CS7nt
ATG TGG CGT CCC TCA GAT TCA ACC GTG TAC GTC CCC CCC CCT AAT CCC
GTG TCC AAA GTC GTC GCT ACC GAC GCC TAC GTC ACC AGG ACA AAT
ATC TTC TAC CAC GCT TCA TCC AGC CGC TTG TTG GCC GTC GGC CAC
CCC TAC TTC AGC ATT AAG CGC GCT AAT AAG ACC GTC GTG CCC AAA
GTC AGC GGC TAC CAG TAC CGC GTC TTC AAA GTG GTC CTC CCC GAC
CCC AAT AAA TTC GCC CTG CCC GAC AGC TCC CTC TTC GAT CCT ACC ACC
CAA AGG CTG GTG TGG GCC TGT ACC GGC CTC GAA GTG GGT CGC GGC
CAG CCC CTG GGT GTC GGC GTC TCC GGC CAC CCC TTC TTG AAT AAG
TAC GAC GAC GTG GAG AAC TCC GGC TCC GGC GGC AAC CCC GGC CAA
GAC AAC CGC GTC AAC GTG GGC ATG GAC TAC AAG CAG ACA CAA TTG
TGC ATG GTC GGT TGC GCC CCC CCC CTG GGC GAG CAC TGG GGC AAA
GGC AAG CAG TGC ACC AAC ACA CCT GTG CAG GCT GGC GAT TGT CCT
CCC CTC GAG TTG ATC ACA TCC GTC ATC CAA GAC GGC GAT ATG GTC
GAC ACC GGT TTC GGC GCC ATG AAC TTC GCC GAT CTG CAG ACA AAC
AAG AGC GAC GTC CCT ATC GAC ATC TGC GGC ACC ACC TGT AAG TAC
CCC GAC TAC CTC CAG ATG GCC GCC GAT CCC TAC GGC GAC CGC CTC
TTC TTC TTC CTC AGG AAA GAG CAG ATG TTC GCC CGC CAT TTC TTC AAC
CGC GCT GGC GAG GTC GGC GAG CCC GTC CCC GAC ACC CTC ATC ATC
AAG GGC TCC GGT AAT CGC ACC AGC GTG GGC TCC TCC ATC TAC GTG
AAC ACC CCC TCC GGT AGC CTC GTC AGC AGC GAA GCC CAG CTG TTC
AAC AAG CCC TAC TGG TTG CAG AAA GCC CAA GGC CAC AAT AAC GGC
ATC TGT TGG GGC AAT CAG CTC TTC GTC ACC GTC GTG GAC ACA ACC
AGG TCC ACC AAC ATG ACC TTG TGC GCC AGC GTC ACC ACC AGC TCC
ACC TAC ACC AAC AGC GAC TAC AAA GAG TAC ATG AGG CAC GTC GAA
GAA TAC GAC CTG CAA TTC ATC TTC CAG CTC TGC TCA ATC ACC CTG AGC
GCC GAG GTG ATG GCT TAC ATC CAT ACC ATG AAC CCC AGC GTC CTC
GAA GAT TGG AAT TTC GGT CTG AGC CCC CCC CCC AAC GGC ACC CTC

-continued

GAA GAC ACC TAC CGC TAC GTG CAA AGC CAA GCT ATC ACA TGC CAA
AAG CCT ACC CCC GAG AAG GAG AAG CCA GAC CCT TAC AAA AAC CTG
TCC TTC TGG GAA GTC AAT CTG AAG GAG AAA TTC AGC TCC GAG CTG
GAC CAA TAC CCT TTG GGC AGG AAA TTC CTG CTC CAG TCC GGC TAC
CGA GGC GGA TCC AGC ATC GCA ACC GGC GTGGAT GGA CCC GCC GTC
AGC AAG GCT AGC GCC GCT CCT AGT GGA AGC GGA GCT GGG ACA AAG
CGT TAAT

SEQ ID No. 17: 6L1CS8nt
ATG TGG CGT CCC TCA GAT TCA ACC GTG TAC GTC CCC CCC CCT AAT CCC
GTG TCC AAA GTC GTC GCT ACC GAC GCC TAC GTC ACC AGG ACA AAT
ATC TTC TAC CAC GCT TCA TCC AGC CGC TTG TTG GCC GTC GGC CAC
CCC TAC TTC AGC ATT AAG CGC GCT AAT AAG ACC GTC GTG CCC AAA
GTC AGC GGC TAC CAG TAC CGC GTC TTC AAA GTG GTC CTC CCC GAC
CCC AAT AAA TTC GCC CTG CCC GAC AGC TCC CTC TTC GAT CCT ACC ACC
CAA AGG CTG GTG TGG GCC TGT ACC GGC CTC GAA GTG GGT CGC GGC
CAG CCC CTG GGT GTC GGC GTC TCC GGC CAC CCC TTC TTG AAT AAG
TAC GAC GAC GTG GAG AAC TCC GGC TCC GGC GGC AAC CCC GGC CAA
GAC AAC CGC GTC AAC GTG GGC ATG GAC TAC AAG CAG ACA CAA TTG
TGC ATG GTC GGT TGC GCC CCC CCC CTG GGC GAG CAC TGG GGC AAA
GGC AAG CAG TGC ACC AAC ACA CCT GTG CAG GCT GGC GAT TGT CCT
CCC CTC GAG TTG ATC ACA TCC GTC ATC CAA GAC GGC GAT ATG GTC
GAC ACC GGT TTC GGC GCC ATG AAC TTC GCC GAT CTG CAG ACA AAC
AAG AGC GAC GTC CCT ATC GAC ATC TGC GGC ACC ACC TGT AAG TAC
CCC GAC TAC CTC CAG ATG GCC GCC GAT CCC TAC GGC GAC CGC CTC
TTC TTC TTC CTC AGG AAA GAG CAG ATG TTC GCC CGC CAT TTC TTC AAC
CGC GCT GGC GAG GTC GGC GAG CCC GTC CCC GAC ACC CTC ATC ATC
AAG GGC TCC GGT AAT CGC ACC AGC GTG GGC TCC TCC ATC TAC GTG
AAC ACC CCC TCC GGT AGC CTC GTC AGC AGC GAA GCC CAG CTG TTC
AAC AAG CCC TAC TGG TTG CAG AAA GCC CAA GGC CAC AAT AAC GGC
ATC TGT TGG GGC AAT CAG CTC TTC GTC ACC GTC GTG GAC ACA ACC
AGG TCC ACC AAC ATG ACC TTG TGC GCC AGC GTC ACC ACC AGC TCC
ACC TAC ACC AAC AGC GAC TAC AAA GAG TAC ATG AGG CAC GTC GAA
GAA TAC GAC CTG CAA TTC ATC TTC CAG CTC TGC TCA ATC ACC CTG AGC
GCC GAG GTG ATG GCT TAC ATC CAT ACC ATG AAC CCC AGC GTC CTC
GAA GAT TGG AAT TTC GGT CTG AGC CCC CCC CCC AAC GGC ACC CTC
GAA GAC ACC TAC CGC TAC GTG CAA AGC CAA GCT ATC ACA TGC CAA
AAG CCT ACC CCC GAG AAG GAG AAG CCA GAC CCT TAC AAA AAC CTG
TCC TTC TGG GAA GTC AAT CTG AAG GAG AAA TTC AGC TCC GAG CTG
GAC CAA TAC CCT TTG GGC AGG AAA TTC CTG CTC CAG TCC GGC TAC
CGA GGC GAC TCC AGC ATC CGA ACC GGC GTG GAT CGA CCC GCC GTC
AGC AAG GCT AGC GCC GCT CCT GAT GCA AAG AGT GCT AAG ACA GGA
CGT TAAT

SEQ ID No. 18: HPV6L1nt
ATG TGG CGT CCC TCA GAT TCA ACC GTG TAC GTC CCC CCC CCT AAT CCC
GTG TCC AAA GTC GTC GCT ACC GAC GCC TAC GTC ACC AGG ACA AAT
ATC TTC TAC CAC GCT TCA TCC AGC CGC TTG TTG GCC GTC GGC CAC
CCC TAC TTC AGC ATT AAG CGC GCT AAT AAG ACC GTC GTG CCC AAA
GTC AGC GGC TAC CAG TAC CGC GTC TTC AAA GTG GTC CTC CCC GAC
CCC AAT AAA TTC GCC CTG CCC GAC AGC TCC CTC TTC GAT CCT ACC ACC
CAA AGG CTG GTG TGG GCC TGT ACC GGC CTC GAA GTG GGT CGC GGC
CAG CCC CTG GGT GTC GGC GTC TCC GGC CAC CCC TTC TTG AAT AAG
TAC GAC GAC GTG GAG AAC TCC GGC TCC GGC GGC AAC CCC GGC CAA
GAC AAC CGC GTC AAC GTG GGC ATG GAC TAC AAG CAG ACA CAA TTG
TGC ATG GTC GGT TGC GCC CCC CCC CTG GGC GAG CAC TGG GGC AAA
GGC AAG CAG TGC ACC AAC ACA CCT GTG CAG GCT GGC GAT TGT CCT
CCC CTC GAG TTG ATC ACA TCC GTC ATC CAA GAC GGC GAT ATG GTC
GAC ACC GGT TTC GGC GCC ATG AAC TTC GCC GAT CTG CAG ACA AAC
AAG AGC GAC GTC CCT ATC GAC ATC TGC GGC ACC ACC TGT AAG TAC
CCC GAC TAC CTC CAG ATG GCC GCC GAT CCC TAC GGC GAC CGC CTC
TTC TTC TTC CTC AGG AAA GAG CAG ATG TTC GCC CGC CAT TTC TTC AAC
CGC GCT GGC GAG GTC GGC GAG CCC GTC CCC GAC ACC CTC ATC ATC
AAG GGC TCC GGT AAT CGC ACC AGC GTG GGC TCC TCC ATC TAC GTG
AAC ACC CCC TCC GGT AGC CTC GTC AGC AGC GAA GCC CAG CTG TTC
AAC AAG CCC TAC TGG TTG CAG AAA GCC CAA GGC CAC AAT AAC GGC
ATC TGT TGG GGC AAT CAG CTC TTC GTC ACC GTC GTG GAC ACA ACC
AGG TCC ACC AAC ATG ACC TTG TGC GCC AGC GTC ACC ACC AGC TCC
ACC TAC ACC AAC AGC GAC TAC AAA GAG TAC ATG AGG CAC GTC GAA
GAA TAC GAC CTG CAA TTC ATC TTC CAG CTC TGC TCA ATC ACC CTG AGC
GCC GAG GTG ATG GCT TAC ATC CAT ACC ATG AAC CCC AGC GTC CTC
GAA GAT TGG AAT TTC GGT CTG AGC CCC CCC CCC AAC GGC ACC CTC
GAA GAC ACC TAC CGC TAC GTG CAA AGC CAA GCT ATC ACA TGC CAA
AAG CCT ACC CCC GAG AAG GAG AAG CCA GAC CCT TAC AAA AAC CTG
TCC TTC TGG GAA GTC AAT CTG AAG GAG AAA TTC AGC TCC GAG CTG
GAC CAA TAC CCT TTG GGC AGG AAA TTC CTG CTC CAG TCC GGC TAC
AGG GGC CGA TCC AGC ATC AGG ACC GGC GTG AAA AGG CCC GCC GTC
AGC AAA GCT AGC GCC GCT CCT AAG AGG AAG AGG GCT AAG ACA AAG
CGT TAAT

-continued

6L1F (SEQ ID No. 19):
5'-GGAATTCGCCGCCACCATGTG-3';

6L1CS1R1 (SEQ ID No. 20):
5'-CCCACGCCGGTTGCGATGCTGGATCGGCCTCCGTAGCCGGACTGGAG
CAGGAATT TCCT-3';

6L1CS1R2 (SEQ ID No. 21):
5'-GCAGGAGCGGCGCTAGCTCCGCTGACGGCGGGTGCTCCCACGCCGGT
TGCGATGC TGGA-3';

6L1CS1R3 (SEQ ID No. 22):
5'-GCTCTAGAATTAACGCTTTGTCCCAGCTGCGGCTCCTGCAGGAGCGG
CGCTAGCT CCGC-3';

6L1CS2R1 (SEQ ID No. 23):
5'-CACGCCGGTTCGGATGCTGGATCCGCCTCGGTAGCCGGACTG 3';

6L1CS2R2 (SEQ ID No. 24):
5'-AGGAGCGGCGCTAGCCTTGCTGACGGCGGGACTTCCCACGCCGGTTC
GGATGCT-3';

6L1CS2R3 (SEQ ID No. 25):
5'-GCTCTAGAATTAACGCTTTGTCCCAGCTCCGCTTCCATCAGGAGCGGC
GCTAGCC TTGC-3';

6L1CS3R1 (SEQ ID No. 26):
5'-CACGCCGGTTCGGATGCTGGATCCGCCTCGGTAGCCGGACTG-3';

6L1CS3R2 (SEQ ID No. 27):
5'-AGGAGCGGCGCTAGCCTTGCTGACGGCGGGTCCATCCACGCCGGTTC
GGATGCT-3';

6L1CS3R3 (SEQ ID No. 28):
5'-GCTCTAGAATTAACGCTTTGTCCCAGCTCTGCTTCCATCAGGAGCGGC
GCTAGCC TTGC-3';

6L1CS4R1 (SEQ ID No. 29):
5'-CACGCCGGTTCGGATGCTGGATCCGCCTCGGTAGCCGGACTG-3';

6L1CS4R2 (SEQ ID No. 30):
5'-AGGAGCGGCGCTAGCCTTGCTGACGGCGGGACTTCCCACGCCGGTTC
GGATGCT-3';

6L1CS4R3 (SEQ ID No. 31):
5'-GCTCTAGAATTAACGCTTTGTATCAGCTCTGCTTCCATCAGGAGCGGC
GCTAGCC TTGC-3';

6L1CS5R1 (SEQ ID No. 32):
5'-CACGCCGGTT CGGATGCTGG ATCCGCCTCG GTAGCCGGAC TG-3';

6L1CS5R2 (SEQ ID No. 33):
5'-AGGAGCGGCGCTAGCCTTGCTGACGGCGGGTCCATCCACGCCGGTTC
GGATGCT-3';

6L1CS5R3 (SEQ ID No. 34):
5'-GCTCTAGAATTAACGCTTTGTATCAGCTCTGCTTCCATCAGGAGCGGC
GCTAGCC TTGC-3';

6L1CS6R1 (SEQ ID No. 35):
5'-CACGCCGGTT CGGATGCTGG ATCCGCCTCG GTAGCCGGAC TG-3';

6L1CS6R2 (SEQ ID No. 36):
5'-AGGAGCGGCGCTAGCACTGCTGACGGCGGGACTTCCCACGCCGGTTC
GGATGCT-3';

6L1CS6R3 (SEQ ID No. 37):
5'-GCTCTAGAATTAACGTCCTGTCCCAGCACCACTTCCACTAGGAGCGGC
GCTAGCA CTGC-3';

6L1CS7R1 (SEQ ID No. 38):
5'-CACGCCGGTT GCGATGCTGG ATCCGCCTCG GTAGCCGGACTG-3';

6L1CS7R2 (SEQ ID No. 39):
5'-AGGAGCGGCGCTAGCCTTGCTGACGGCGGGTCCATCCACGCCGGTTG
CGATGCT-3';

6L1CS7R3 (SEQ ID No. 40):
5'-GCTCTAGAATTAACGCTTTGTCCCAGCTCCGCTTCCACTAGGAGCGGC
GCTAGCC TTGC-3';

6L1CS8R1 (SEQ ID No. 41):
5'-CACGCCGGTT CGGATGCTGG AGTCGCCTCG GTAGCCGGAC TG-3';

6L1CS8R2 (SEQ ID No. 42):
5'-AGGAGCGGCGCTAGCCTTGCTGACGGCGGGTCGATCCACGCCGGTTC
GGATGCT-3';

6L1CS8R3 (SEQ ID No. 43):
5'-GCTCTAGAATTAACGTCCTGTCTTAGCACTCTTTGCATCAGGAGCGGC
GCTAGCC TTGC-3'.

What claimed is:

1. A C-terminus modified HPV6 L1 protein, which is as shown in the sequence selected from the group consisting of: SEQ ID No. 2, SEQ ID No. 3, SEQ ID No. 4, SEQ ID No. 5, SEQ ID No. 6, SEQ ID No. 7, SEQ ID No. 8 and SEQ ID No. 9.

2. A polynucleotide encoding the C-terminus modified HPV6 L1 protein according to claim 1.

3. The polynucleotide according to claim 2, wherein the sequence of the polynucleotide is whole-gene optimized using insect cell codons.

4. The polynucleotide according to claim 2, wherein the polynucleotide is the sequence selected from the group consisting of: SEQ ID No. 10, SEQ ID No. 11, SEQ ID No. 12, SEQ ID No. 13, SEQ ID No. 14, SEQ ID No. 15, SEQ ID No. 16 and SEQ ID No. 17.

5. A vector comprising the polynucleotide according to claim 2.

6. The vector of claim 5, wherein the vector is selected from the group consisting of: a plasmid, a recombinant Bacmid and a recombinant baculovirus.

7. A host cell comprising the vector according to claim 5.

8. The host cell of claim 7, wherein the host cell is selected from the group consisting of: *E. coli*, yeast cell and insect cell.

9. A multimer wherein:

the multimer is a pentamer or a virus-like particle;

the multimer comprises or is formed by the C-terminus modified HPV6 L1 protein according to claim 1.

10. A vaccine for preventing a papillomavirus infection or related disease thereof, the vaccine comprising:

the multimer according to claim 9, an adjuvant; and an excipient or vaccine carrier.

11. The vaccine of claim 10, wherein the adjuvant is suitable for human use.

12. The vaccine of claim 11, further comprising: mucosa-tropic HPV virus-like particle; skin-tropic HPV virus-like particle; or combinations thereof.

* * * * *